United States Patent [19]
Alves et al.

[11] Patent Number: 5,693,496
[45] Date of Patent: Dec. 2, 1997

[54] DNA ENCODING THE MOUSE AND HUMAN PH30 BETA CHAIN PROTEIN

[75] Inventors: Kenneth Alves, Manalapan; Gregory Franklin Hollis, Westfield; Sunil K. Gupta, Piscataway, all of N.J.

[73] Assignee: Merck & Co., Inc., Rahway, N.J.

[21] Appl. No.: 264,101

[22] Filed: Jun. 20, 1994

[51] Int. Cl.⁶ .............................. C12N 15/12; C12N 15/63
[52] U.S. Cl. .............. 435/69.3; 435/252.3; 435/252.33; 435/254.11; 435/255.1; 435/320.1; 435/254.2; 536/235
[58] Field of Search ........................ 435/69.3, 252.3, 435/320.1, 252.33, 254.11, 255.7, 254.2; 536/23.5

[56] References Cited

U.S. PATENT DOCUMENTS 4,879,213  11/1989  Fox et al.

FOREIGN PATENT DOCUMENTS

93/25233  12/1993  WIPO.

OTHER PUBLICATIONS

Journal of Cell Biol., Primakoff et al., Identification & Purification of a Sperm Surface Protein vol. 104, Jan. 1987, pp. 141–149.

Nature, Blobel et al., A potential fusion peptide and an integrin ligand domain in a protein active in sperm–egg fusion, vol. 356, 19 Mar. 1992.

Journal of Cell. Biol., Blobel et al., Proteolytic Processing of a Protein involved in Sperm–Egg Fusion, vol. 111, Jul. 1990, pp. 69–78.

Proc. Natl. Acad. Sci., Myles et al., Identification of a binding site in the disintegrin domain of fertilin required for sperm–egg fusion, USA, vol. 91, pp. 4195–4198.

Bowie et al. Science 247:1306–1310 Mar. 1990.

Kumar et al PNAS 87:1337–1341 1990.

Smith et al Mol. Cell Biology 3(12):2156–2165 1983.

Pennock et al. Mol. Cell Biology 4(3):399–406 Mar. 1984.

*Primary Examiner*—Anthony C. Caputa
*Attorney, Agent, or Firm*—Mary A. Appollina; Melvin Winokur

[57] ABSTRACT

The instant invention is drawn to a DNA encoding a sperm surface protein in substantially pure form selected from a human PH30 beta chain protein and a mouse PH30 beta chain proteins. Such proteins are useful as contraceptive vaccines in humans and mice respectively, and for identifying small molecules that will disrupt sperm-egg interaction and fertilization.

8 Claims, 31 Drawing Sheets

```
      10              30              50
       .               .               .
  1 GGCCAAGATTTTCAGAATTTCTGCCACTACCAAGGGTATATTGAAGGTTATCCAAAATCT 60
    GlyGlnAspPheGlnAsnPheCysHisTyrGlnGlyTyrIleGluGlyTyrProLysSer 70              90             110
       .               .               .
 61 GTGGTGATGGTTAGCACATGTACTGGACTCAGGGGCGTACTACAGTTTGAAAATGTTAGT 120
    ValValMetValSerThrCysThrGlyLeuArgGlyValLeuGlnPheGluAsnValSer 130             150             170
       .               .               .
121 TATGGAATAGAACCCCTGGAGTCTTCAGTTGGCTTTGAACATGTAATTTACCAAGTAAAA 180
    TyrGlyIleGluProLeuGluSerSerValGlyPheGluHisValIleTyrGlnValLys 190             210             230
       .               .               .
181 CATAAGAAAGCAGATGTTTCCTTATATAATGAGAAGGATATTGAATCAAGAGATCTGTCC 240
    HisLysLysAlaAspValSerLeuTyrAsnGluLysAspIleGluSerArgAspLeuSer 250             270             290
       .               .               .
241 TTTAAATTACAAAGCGCAGAGCCACAGCAAGATTTTGCAAAGTATATAGAAATGCATGTT 300
    PheLysLeuGlnSerAlaGluProGlnGlnAspPheAlaLysTyrIleGluMetHisVal 310             330             350
       .               .               .
301 ATAGTTGAAAAACAATTGTATAATCATATGGGGTCTGATACAACTGTTGTCGCTCAAAAA 360
    IleValGluLysGlnLeuTyrAsnHisMetGlySerAspThrThrValValAlaGlnLys
```

FIG.1A

```
            370              390              410
              .                .                .
361  GTTTTCCAGTTGATTGGATTGACGAATGCTATTTTTGTTTCATTTAATATTACAATTATT  420
     ValPheGlnLeuIleGlyLeuThrAsnAlaIlePheValSerPheAsnIleThrIleIle 430              450              470
              .                .                .
421  CTGTCTTCATTGGAGCTTTGGATAGATGAAAATAAAATTGCAACCACTGGAGAAGCTAAT  480
     LeuSerSerLeuGluLeuTrpIleAspGluAsnLysIleAlaThrThrGlyGluAlaAsn 490              510              530
              .                .                .
481  GAGTTATTACACACATTTTTAAGATGGAAAACATCTTATCTTGTTTTACGTCCTCATGAT  540
     GluLeuLeuHisThrPheLeuArgTrpLysThrSerTyrLeuValLeuArgProHisAsp 550              570              590
              .                .                .
541  GTGGCATTTTTACTTGTTTACAGAGAAAAGTCAAATTATGTTGGTGCAACCTTTCAAGGG  600
     ValAlaPheLeuLeuValTyrArgGluLysSerAsnTyrValGlyAlaThrPheGlnGly 610              630              650
              .                .                .
601  AAGATGTGTGATGCAAACTATGCAGGAGGTGTTGTTCTGCACCCCAGAACCATAAGTCTG  660
     LysMetCysAspAlaAsnTyrAlaGlyGlyValValLeuHisProArgThrIleSerLeu 670              690              710
              .                .                .
661  GAATCACTTGCAGTTATTTTAGCTCAATTATTGAGCCTTAGTATGGGGATCACTTATGAT  720
     GluSerLeuAlaValIleLeuAlaGlnLeuLeuSerLeuSerMetGlyIleThrTyrAsp
```

FIG. 1B

```
        730              750              770
         .                .                .
         .                .                .
721 GACATTAACAAATGCCAGTGCTCAGGAGCTGTCTGCATTATGAATCCAGAAGCAATTCAT 780
    AspIleAsnLysCysGlnCysSerGlyAlaValCysIleMetAsnProGluAlaIleHis 790              810              830
         .                .                .
         .                .                .
781 TTCAGTGGTGTGAAGATCTTTAGTAACTGCAGCTTCGAAGACTTTGCACATTTTATTTCA 840
    PheSerGlyValLysIlePheSerAsnCysSerPheGluAspPheAlaHisPheIleSer 850              870              890
         .                .                .
         .                .                .
841 AAGCAGAAGTCCCAGTGTCTTCACAATCAGCCTCGCTTAGATCCTTTTTTCAAACAGCAA 900
    LysGlnLysSerGlnCysLeuHisAsnGlnProArgLeuAspProPhePheLysGlnGln 910              930              950
         .                .                .
         .                .                .
901 GCAGTGTGTGGTAATGCAAAGCTGGAAGCAGGAGAGGAGTGTGACTGTGGGACTGAACAG 960
    AlaValCysGlyAsnAlaLysLeuGluAlaGlyGluGluCysAspCysGlyThrGluGln 970              990             1010
         .                .                .
         .                .                .
961 GATTGTGCCCTTATTGGAGAAACATGCTGTGATATTGCCACATGTAGATTTAAAGCCGGT 1020
    AspCysAlaLeuIleGlyGluThrCysCysAspIleAlaThrCysArgPheLysAlaGly 1030             1050             1070
         .                .                .
         .                .                .
1021 TCAAACTGTGCTGAAGGACCATGCTGCGAAAACTGTCTATTTATGTCAAAAGAAAGAATG 1080
    SerAsnCysAlaGluGlyProCysCysGluAsnCysLeuPheMetSerLysGluArgMet
```

FIG.1C

```
              1090              1110              1130
               .                 .                 .
1081  TGTAGGCCTTCCTTTGAAGAATGCGACCTCCCTGAATATTGCAATGGATCATCTGCATCA  1140
      CysArgProSerPheGluGluCysAspLeuProGluTyrCysAsnGlySerSerAlaSer 1150              1170              1190
               .                 .                 .
1141  TGCCCAGAAAACCACTATGTTCAGACTGGGCATCCGTGTGGACTGAATCAATGGATCTGT  1200
      CysProGluAsnHisTyrValGlnThrGlyHisProCysGlyLeuAsnGlnTrpIleCys 1210              1230              1250
               .                 .                 .
1201  ATAGATGGAGTTTGTATGAGTGGGGATAAACAATGTACAGACACATTTGGCAAAGAAGTA  1260
      IleAspGlyValCysMetSerGlyAspLysGlnCysThrAspThrPheGlyLysGluVal 1270              1290              1310
               .                 .                 .
1261  GAGTTTGGCCCTTCAGAATGTTATTCTCACCTTAATTCAAAGACTGATGTATCTGGAAAC  1320
      GluPheGlyProSerGluCysTyrSerHisLeuAsnSerLysThrAspValSerGlyAsn 1330              1350              1370
               .                 .                 .
1321  TGTGGTATAAGTGATTCAGGATACACACAGTGTGAAGCTGACAATCTGCAGTGCGGAAAA  1380
      CysGlyIleSerAspSerGlyTyrThrGlnCysGluAlaAspAsnLeuGlnCysGlyLys 1390              1410              1430
               .                 .                 .
1381  TTAATATGTAAATATGTAGGTAAATTTTTATTACAAATTCCAAGAGCCACTATTATTTAT  1440
      LeuIleCysLysTyrValGlyLysPheLeuLeuGlnIleProArgAlaThrIleIleTyr
```

FIG. 1D

```
          1450              1470              1490
           .                 .                 .
1441  GCCAACATAAGTGGACATCTCTGCATTGCTGTGGAATTTGCCAGTGATCATGCAGACAGC  1500
      AlaAsnIleSerGlyHisLeuCysIleAlaValGluPheAlaSerAspHisAlaAspSer 1510              1530              1550
           .                 .                 .
1501  CAAAAGATGTGGATAAAAGATGGAACTTCTTGTGGTTCAAATAAGGTTTGCAGGAATCAA  1560
      GlnLysMetTrpIleLysAspGlyThrSerCysGlySerAsnLysValCysArgAsnGln 1570              1590              1610
           .                 .                 .
1561  AGATGTGTGAGTTCTTCATACTTGGGTTATGATTGTACTACTGACAAATGCAATGATAGA  1620
      ArgCysValSerSerSerTyrLeuGlyTyrAspCysThrThrAspLysCysAsnAspArg 1630              1650              1670
           .                 .                 .
1621  GGTGTATGCAATAACAAAAAGCACTGTCACTGTAGTGCTTCATATTTACCTCCAGATTGC  1680
      GlyValCysAsnAsnLysLysHisCysHisCysSerAlaSerTyrLeuProProAspCys 1690              1710              1730
           .                 .                 .
1681  TCAGTTCAATCAGATCTATGGCCTGGTGGGAGTATTGACAGTGGCAATTTTCCACCTGTA  1740
      SerValGlnSerAspLeuTrpProGlyGlySerIleAspSerGlyAsnPheProProVal 1750              1770              1790
           .                 .                 .
1741  GCTATACCAGCCAGACTCCCTGAAAGGCGCTACATTGAGAACATTTACCATTCCAAACCA  1800
      AlaIleProAlaArgLeuProGluArgArgTyrIleGluAsnIleTyrHisSerLysPro
```

FIG.1E

```
            1810           1830           1850
              .     .        .     .        .     .
1801 ATGAGATGGCCATTTTTCTTATTCATTCCTTTCTTTATTATTTTCTGTGTACTGATTGCT 1860
     MetArgTrpProPhePheLeuPheIleProPhePheIleIlePheCysValLeuIleAla 1870           1890           1910
              .     .        .     .        .     .
1861 ATAATGGTGAAAGTTAATTTCCAAAGGAAAAAATGGAGAACTGAGGACTATTCAAGCGAT 1920
     IleMetValLysValAsnPheGlnArgLysLysTrpArgThrGluAspTyrSerSerAsp 1930           1950           1970
              .     .        .     .        .     .
1921 GAGCAACCTGAAAGTGAGAGTGAACCTAAAGGGTAGTCTGGACAACAGAGATGCCATGAT 1980
     GluGlnProGluSerGluSerGluProLysGly 1990           2010           2030
              .     .        .     .        .     .
1981 ATCACTTCTTCTAGAGTAATTATCTGTGATGGATGGACACAAAAAAAATGGAAAGAAAAGA 2040

2050           2070           2090
              .     .        .     .        .     .
2041 ATGTACATTACCTGGTTTCCTGGGATTCAAACCTGCATATTGTGATTTTAATTTGACCAG 2100

2110           2130           2150
              .     .        .     .        .     .
2101 AAAATATGATATATATGTATAATTTCACAGATAATTTACTTATTTAAAAATGCATGATAA 2160
```

2161  TGAGTTTTACATTACAAATTTCTGTTTTTTTAAAGTTATCTTACGCTATTTCTGTTGGTT  2220

2230              2250              2270

2221  AGTAGACACTAATTCTGTCAGTAGGGGCATGGTATAAGGAAATATCATAATGTAATGAGG  2280

2290              2310              2330

2281  TGGTACTATGATTAAAAGCCACTGTTACATTTCAAAAAAAAAAAAAAAA  2330
```

1  GGCACGAGCGATTATGTTGGCGCTACCTATCAAGGGAACATGTGTGACAAGAACTATGCA  60

GlyThrSerAspTyrValGlyAlaThrTyrGlnGlyLysMetCysAspLysAsnTyrAla 70              90             110
           .               .               .

61  GGAGGAGTTGCTTTGCACCCCAAAGCCGTAACTCTGGAATCACTTGCAATTATTTTAGTT 120

GlyGlyValAlaLeuHisProLysAlaValThrLeuGluSerLeuAlaIleIleLeuVal 130             150             170
           .               .               .

121  CAGCTGCTGAGCCTCAGCATGGGGCTAGCGTATGACGACGTGAACAAGTGCCAGTGTGGC 180

GlnLeuLeuSerLeuSerMetGlyLeuAlaTyrAspAspValAsnLysCysGlnCysGly 190             210             230
           .               .               .

181  GTACCTGTCTGCGTGATGAACCCGGAAGCGCCTCACTCCAGCGGTGTCCGGGCCTTCAGT 240

ValProValCysValMetAsnProGluAlaProHisSerSerGlyValArgAlaPheSer 250             270             290
           .               .               .

241  AACTGCAGCATGGAGGACTTTTCCAAGTTTATCACAAGTCAAAGCTCCCACTGTCTGCAG 300

AsnCysSerMetGluAspPheSerLysPheIleThrSerGlnSerSerHisCysLeuGln 310             330             350
           .               .               .

301  AACCAGCCAACGCTACAGCCATCTTACAAGATGGCCGTCTGTGGGAATGGAGAGGTGGAA 360

AsnGlnProThrLeuGlnProSerTyrLysMetAlaValCysGlyAsnGlyGluValGlu
```

361   GAAGATGAAATTTGCGACTGTGGAAAGAAGGGCTGTGCAGAAATGCCCCCGCCATGCTGT   420

GluAspGluIleCysAspCysGlyLysLysGlyCysAlaGluMetProProProCysCys 430              450              470
           .                .                .

421   AACCCCGACACCTGTAAGCTGTCAGATGGCTCCGAGTGCTCCAGCGGGATATGCTGCAAC   480

AsnProAspThrCysLysLeuSerAspGlySerGluCysSerSerGlyIleCysCysAsn 490              510              530
           .                .                .

481   TCGTGCAAGCTGAAGCGGAAAGGGGAGGTTTGCAGGCTTGCCCAAGATGAGTGTGATGTC   540

SerCysLysLeuLysArgLysGlyGluValCysArgLeuAlaGlnAspGluCysAspVal 550              570              590
           .                .                .

541   ACAGAGTACTGCAACGGCACATCCGAAGTGTGTGAAGACTTCTTTGTTCAAAACGGTCAC   600

ThrGluTyrCysAsnGlyThrSerGluValCysGluAspPhePheValGlnAsnGlyHis 610              630              650
           .                .                .

601   CCATGTGACAATCGCAAGTGGATCTGTATTAACGGCACCTGTCAGAGTGGAGAACAGCAG   660

ProCysAspAsnArgLysTrpIleCysIleAsnGlyThrCysGlnSerGlyGluGlnGln 670              690              710
           .                .                .

661   TGCCAGGATCTATTTGGCATCGATGCAGGCTTTGGTTCAAGTGAATGTTTCTGGGAGCTG   720

CysGlnAspLeuPheGlyIleAspAlaGlyPheGlySerSerGluCysPheTrpGluLeu
```

721  AATTCCAAGAGCGACATATCTGGGAGCTGTGGAATCTCTGCTGGGGGATACAAGGAATGC 780

AsnSerLysSerAspIleSerGlySerCysGlyIleSerAlaGlyGlyTyrLysGluCys 790                 810                 830
                 .                   .                   .
                 .                   .                   .

781  CCACCTAATGACCGGATGTGTGGGAAAATAATATGTAAATACCAAAGTGAAAATATACTA 840

ProProAsnAspArgMetCysGlyLysIleIleCysLysTyrGlnSerGluAsnIleLeu 850                 870                 890
                 .                   .                   .
                 .                   .                   .

841  AAATTGAGGTCTGCCACTGTTATTTATGCCAATATAAGCGGGCATGTCTGCGTTTCCCTG 900

LysLeuArgSerAlaThrValIleTyrAlaAsnIleSerGlyHisValCysValSerLeu 910                 930                 950
                 .                   .                   .
                 .                   .                   .

901  GAATATCCCCAAGGTCATAATGAGAGCCAGAAGATGTGGGTGAGAGATGGAACCGTCTGC 960

GluTyrProGlnGlyHisAsnGluSerGlnLysMetTrpValArgAspGlyThrValCys 970                 990                1010
                 .                   .                   .
                 .                   .                   .

961  GGGTCAAATAAGGTTTGCCAGAATCAAAAATGTGTAGCAGACACTTTCTTGGGCTATGAT 1020

GlySerAsnLysValCysGlnAsnGlnLysCysValAlaAspThrPheLeuGlyTyrAsp 1030                1050                1070
                 .                   .                   .
                 .                   .                   .

1021 TGCAACCTGGAAAAATGCAACCACCATGGTGTATGTAATAACAAGAAGAACTGCCACTGT 1080

CysAsnLeuGluLysCysAsnHisHisGlyValCysAsnAsnLysLysAsnCysHisCys
```

FIG.2C

```
        1090               1110                1130
1081  GACCCCACATACTTACCTCCAGATTGTAAAAGAATGAAAGATTCATATCCTGGCGGGAGC  1140
      AspProThrTyrLeuProProAspCysLysArgMetLysAspSerTyrProGlyGlySer 1150               1170                1190
1141  ATTGATAGTGGCAACAAGGAAAGGGCTGAACCCATCCCTGTACGGCCCTACATTGCAAGT  1200
      IleAspSerGlyAsnLysGluArgAlaGluProIleProValArgProTyrIleAlaSer 1210               1230                1250
1201  CGTTACCGCTCCAAGTCTCCACGGTGGCCATTTTTCTTGATCATCCCTTTCTACGTTGTG  1260
      ArgTyrArgSerLysSerProArgTrpProPhePheLeuIleIleProPheTyrValVal 1270               1290                1310
1261  ATCCTTGTCCTGATTGGGATGCTGGTAAAAGTCTATTCCCAAAGGATGAAATGGAGAATG  1320
      IleLeuValLeuIleGlyMetLeuValLysValTyrSerGlnArgMetLysTrpArgMet 1330               1350                1370
1321  GATGACTTCTCAAGCGAAGAGCAATTTGAAAGTGAAAGTGAATCCAAAGACTAGTCTGGA  1380
      AspAspPheSerSerGluGluGlnPheGluSerGluSerGluSerLysAsp 1390               1410                1430
1381  CAGATTCCACAATGTCACAAGTAATTCTCTTCAGTGGACAGAAAAAAAAGTGGAAAAGAA  1440

1450               1470                1490
1441  AAGCCTATGCATTATCTTGCCTGAAAGTCAAGCCTGCATATCGTGGTCTCCATCAGGCCA  1500

1510               1530                1550
1501  GAAATCATATCTCTCCATTACACATGTATGATACATATGTGTGTATATTATTCCATAAAT  1560
```

FIG. 2D

```
                  1570              1590              1610
1561  GATTTACTTGTAAGAAATGAATGATTATGAATTTCATATTATACTTTGATATTTTACCCT  1620

1630              1650              1670
1621  ATTTCTGGTAGTCGGTAGTCATCAATTGTATTTTCTAGTAGGTACATTATAGAAAAGGCT  1680

1690
1681  ATAAGAAAATAAATGTGGTACCA  1703
```

FIG.2E

```
         T
  H      s
  Ca     p         B
  ve     A5        sS
  iI     p0        at
  JI     o9        Jy
  II     II        II
   /      /         /
GGCCAAGATTTTCAGAATTTCTGCCACTACCAAGGGTATATTGAAGGTTATCCAAAATCT
1 ————+————+————+————+————+————+ 60
CCGGTTCTAAAAGTCTTAAAGACGGTGATGGTTCCCATATAACTTCCAATAGGTTTTAGA

B
            s
            Ap   N
            fL   I       BH
   B        HIU  oNPR   siBD       M   R S
   c        pII  IsIs   pnsd       I   s f
   c        hII  Ipea   Gfre       y   o c
   I        III  IIII   IIII       I   I I
             /    ///     /
GTGGTGATGGTTAGCACATGTACTGGACTCAGGGGCGTACTACAGTTTGAAAATGTTAGT
61 ————+————+————+————+————+————+ 120
CACCACTACCAATCGTGTACATGACCTGAGTCCCCGCATGATGTCAAACTTTTACAATCA B
                                        s    T
       E                                Ap   N s
       c      E                         fL   I p
       o      BcMSH              C      IU   oN5
       5      MBsobci      P     v    B II   IsO
       7      IboRorn      I     i    p II   Ip9
              ysJIIFf      e     J    m II   III
       I      IIIIIII      I     I    I II   III
                ////                   /      //
TATGGAATAGAACCCCTGGAGTCTTCAGTTGGCTTTGAACATGTAATTTACCAAGTAAAA
121 ————+————+————+————+————+————+ 180
ATACCTTATCTTGGGGACCTCAGAAGTCAACCGAAACTTGTACATTAAATGGTTCATTTT S
                                       H      BB a
                                       iT     gsDu
                                       nf     Itp3
                                       fi     IYnA
                                       II     IIII
                                        /      //
CATAAGAAAGCAGATGTTTCCTTATATAATGAGAAGGATATTGAATCAAGAGATCTGTCC
181 ————+————+————+————+————+————+ 240
GTATTCTTTCGTCTACAAAGGAATATATTACTCTTCCTATAACTTAGTTCTCTAGACAGG
```

FIG. 3A

```
                        T
                        s
                        p                               N
                        M05         C           C       I
                        sr0   H     v           v       C   N aN
                        ea9   h     i           i       v   i Is
                        III   a     J           R       s   i Ip
                              I     I           I       R   I II
                                                        I
     TTTAAATTACAAAGCGCAGAGCCACAGCAAGATTTTGCAAAGTATATAGAAATGCATGTT
 241 ─────────┼─────────┼─────────┼─────────┼─────────┼─────────┼ 300
     AAATTTAATGTTTCGCGTCTCGGTGTCGTTCTAAAACGTTTCATATATCTTTACGTACAA
```

```
              T
              s
              p
              M5          N           B
              u0          d           a
              n9          e           e
              II          I           I

ATAGTTGAAAAACAATTGTATAATCATATGGGGTCTGATACAACTGTTGTCGCTCAAAAA
 301 ─────────┼─────────┼─────────┼─────────┼─────────┼─────────┼ 360
     TATCAACTTTTTGTTAACATATTAGTATACCCCAGACTATGTTGACAACAGCGAGTTTTT
```

```
                                                        T
                                                        s
              B                                         p    M
          B   s             B           M    S          5    Bb
          s   t             s           s    s          0    bo
          r   X             m           e    p          9    sI
          I   I             I           I    I          I    II

GTTTTCCAGTTGATTGGATTGACGAATGCTATTTTTGTTTCATTTAATATTACAATTATT
 361 ─────────┼─────────┼─────────┼─────────┼─────────┼─────────┼ 420
     CAAAAGGTCAACTAACCTAACTGCTTACGATAAAAACAAAGTAAATTATAATGTTAATAA
```

```
                                   T
                                   s
              C                    p    C                C
              Av                   5    v        B       Av
              Ii                   0    i        s       Ii
              uJ                   9    R        r       uJ
              II                   I    I        I       II

CTGTCTTCATTGGAGCTTTGGATAGATGAAAATAAAATTGCAACCACTGGAGAAGCTAAT
 421 ─────────┼─────────┼─────────┼─────────┼─────────┼─────────┼ 480
     GACAGAAGTAACCTCGAAACCTATCTACTTTTATTTTAACGTTGGTGACCTCTTCGATTA
```

FIG.3B

```
                                          M
                                          a          N
                                          e          l
   B         M       B                    I    R     a
   p         s       c                    |    c     I
   m         e       c                    |    a     I
   I         I       I                    I    I     I
   GAGTTATTACACACATTTTAAGATGGAAAACATCTTATCTTGTTTTACGTCCTCATGAT
481 ─────────┼─────────┼─────────┼─────────┼─────────┼─────────+ 540
   CTCAATAATGTGTGTAAAAATTCTACCTTTTGTAGAATAGAACAAAATGCAGGAGTACTA
```

```
                            T
                            s
                            p
                            5              C                   S
                            0              v         B         f
   M                        9              i         s         a
   n                        I              R         I         N
   I                        I              I         I         I
   GTGGCATTTTTACTTGTTTACAGAGAAAAGTCAAATTATGTTGGTGCAACCTTTCAAGGG
541 ─────────┼─────────┼─────────┼─────────┼─────────┼─────────+ 600
   CACCGTAAAAATGAACAAATGTCTCTTTTCAGTTTAATACAACCACGTTGGAAAGTTCCC
```

```
       MC      A  C              C         D         B
       bv      MpMBv             v         r         s
       oi      nowsi             i         d         t
       IR      IBogR             R         I         X
       II      IIIII             I         I         I
              / /
   AAGATGTGTGATGCAAACTATGCAGGAGGTGTTGTTCTGCACCCCAGAACCATAAGTCTG
601 ─────────┼─────────┼─────────┼─────────┼─────────┼─────────+ 660
   TTCTACACACTACGTTTGATACGTCCTCCACAACAAGACGTGGGGTCTTGGTATTCAGAC
```

```
                         T
                         s                      S
                         p                      a
   H       C       C     p      C               u    D
   iT      v       Av    5      v  D     B      3    p     A
   nf      i       li    0      i  d     s      A    n     l
   fi      R       uJ    9      J  e     I      I    I     w
   II      I       II    I      I  I     I      I    I     I
   /                    /
   GAATCACTTGCAGTTATTTTAGCTCAATTATTGAGCCTTAGTATGGGGATCACTTATGAT
661 ─────────┼─────────┼─────────┼─────────┼─────────┼─────────+ 720
   CTTAGTGAACGTCAATAAAATCGAGTTAATAACTCGGAATCATACCCCTAGTGAATACTA
```

```
                          B
                          s
                          p                            B
                          1            N               s
              B           2           N              Ap  N              BC
              s           8          aN              fL  I              svM
              m           6          Is              IU  aN      MD     ris
              F           I          Ip              Is  Is      sr     FJp
              I                      II              Ip  Ip      ea     III
                                                     II  II      II
                GATTGTGCCCTTATTGGAGAAACATGCTGTGATATTGCCACATGTAGATTTAAAGCCGGT
           961 ─────┼─────┼─────┼─────┼─────┼─────┼ 1020
                CTAACACGGGAATAACCTCTTTGTACGACACTATAACGGTGTACATCTAAATTTCGGCCA
```

```
                            S       NF        E
                            Aa      In        c
               B            vu      ou        o
               b            a9      I4        5
               v            I6      IH        7
               I            II      II        I

TCAAACTGTGCTGAAGGACCATGCTGCGAAAACTGTCTATTTATGTCAAAAGAAAGAATG
           1021 ─────┼─────┼─────┼─────┼─────┼─────┼ 1080
                AGTTTGACACGACTTCCTGGTACGACGCTTTTGACAGATAAATACAGTTTTCTTTCTTAC
```

```
                  H                                         S
                C a                     M            C      a B         C
                vHeS        B  b       MS  v        u sD    Av
                ialt        s  o       ns  i        3 rp    li
                Jelu        m  l       Ip  R      A Dn      wR
                IIII        I  I       II  I      I II      II
                TGTAGGCCTTCCTTTGAAGAATGCGACCTCCCTGAATATTGCAATGGATCATCTGCATCA
           1081 ─────┼─────┼─────┼─────┼─────┼─────┼ 1140
                ACATCCGGAAGGAAACTTCTTACGCTGGAGGGACTTATAACGTTACCTAGTAGACGTAGT
```

```
                 N                                                 S
                 I  S                         S     H              Ba
                 a  f         F        B  M   f     iT             suD
                 I  a         o        s  s   a     nf             t3p
                 I  N         k        r  I   N     fi             YAn
                 I  I         I        I  I   I     II             III
                TGCCCAGAAAACCACTATGTTCAGACTGGGCATCCGTGTGGACTGAATCAATGGATCTGT
           1141 ─────┼─────┼─────┼─────┼─────┼─────┼ 1200
                ACGGGTCTTTTGGTGATACAAGTCTGACCCGTAGGCACACCTGACTTAGTTACCTAGACA
```

FIG. 3E

```
                                    B
                                    s
                                    p
                                    1                              E
                                    4  R                           c
         A    B                     0  s                           o
         l    c                     7  a                           5
         w    c                     l  l                           7
         l    l                     l  l                           l
         ATAGATGGAGTTTGTATGAGTGGGGATAAACAATGTACAGACACATTTGGCAAAGAAGTA
    1201 ─────┼─────────┼─────────┼─────────┼─────────┼─────────┼ 1260
         TATCTACCTCAAACATACTCACCCCTATTTGTTACATGTCTGTGTAAACCGTTTCTTCAT

T
         S H                        s
         a C a                      p
         u v e            H         M5                  B
         9 i l            p         s 0                 a
         6 J l            h         e 9                 e
         l l l            l         l l                 l
              /
         GAGTTTGGCCCCTTCAGAATGTTATTCTCACCTTAATTCAAAGACTGATGTATCTGGAAAC
    1261 ─────┼─────────┼─────────┼─────────┼─────────┼─────────┼ 1320
         CTCAAACCGGGAAGTCTTACAATAAGAGTGGAATTAAGTTTCTGACTACATAGACCTTTG

T
                             D D                                    s
               H             r r          C                         p
               i T           a a          A v      S v P    A       5
               n f           l l          l i      f i s    c       0
               f i           l l          u J      c R t    i       9
               l l           l l          l l      l l l    l       l
                                          /
         TGTGGTATAAGTGATTCAGGATACACACAGTGTGAAGCTGACAATCTGCAGTGCGGAAAA
    1321 ─────┼─────────┼─────────┼─────────┼─────────┼─────────┼ 1380
         ACACCATATTCACTAAGTCCTATGTGTGTCACACTTCGACTGTTAGACGTCACGCCTTTT

T         T
                          s         s
                          p         p
                          A 5       A 5       C
         M V              p 0       p 0       v
         s s              o 9       o 9       i
         e p              l l       l l       J
         l l              l l       l l       l
              /                /          /
         TTAATATGTAAATATGTAGGTAAATTTTTATTACAAATTCCAAGAGCCACTATTATTTAT
    1381 ─────┼─────────┼─────────┼─────────┼─────────┼─────────┼ 1440
         AATTATACATTTATACATCCATTTAAAAATAATGTTTAAGGTTCTCGGTGATAATAAATA
```

FIG. 3F

```
                                    T
                                    s
                                    p                    S          N
                     BC             a                    a          Cl         C
                     sv    M        A5        B         BuD         vo         v
                     ri    s        p0        s         c3p         il         i
                     DR    I        o9        r         lAn         RI         J
                     II    I        II        I         III         II         I
                          /         /                    /           /
         GCCAACATAAGTGGACATCTCTGCATTGCTGTGGAATTTGCCAGTGATCATGCAGACAGC
    1441 ─────────┼─────────┼─────────┼─────────┼─────────┼─────────┼ 1500
         CGGTTGTATTCACCTGTAGAGACGTAACGACACCTTAAACGGTCACTAGTACGTCTGTCG

D                     C          H
                     B                        r                     v          iT
                     c                        d                     i          nf
                     c                        I                     R          fi
                     I                        I                     I          II
                                                                              /
         CAAAAGATGTGGATAAAAGATGGAACTTCTTGTGGTTCAAATAAGGTTTGCAGGAATCAA
    1501 ─────────┼─────────┼─────────┼─────────┼─────────┼─────────┼ 1560
         GTTTTCTACACCTATTTTCTACCTTGAAGAACACCAAGTTTATTCCAAACGTCCTTAGTT

M                                                C          B
             b                                                vM         s
             o                                     R          in         r
             I                                     s          RI         D
             I                                     o          II         I
                                                   I
         AGATGTGTGAGTTCTTCATACTTGGGTTATGATTGTACTACTGACAAATGCAATGATAGA
    1561 ─────────┼─────────┼─────────┼─────────┼─────────┼─────────┼ 1620
         TCTACACACTCAAGAAGTATGAACCCAATACTAACATGATGACTGTTTACGTTACTATCT

M T
                          a s
             C            e p    S M  B
             v            l 4    f s  p                                  MD
             i            l 5    c I  m                                  nd
             R            I I    I I  I                                  le
             I                                                           II
         GGTGTATGCAATAACAAAAAGCACTGTCACTGTAGTGCTTCATATTTACCTCCAGATTGC
    1621 ─────────┼─────────┼─────────┼─────────┼─────────┼─────────┼ 1680
         CCACATACGTTATTGTTTTTCGTGACAGTGACATCACGAAGTATAAATGGAGGTCTAACG
```

FIG. 3G

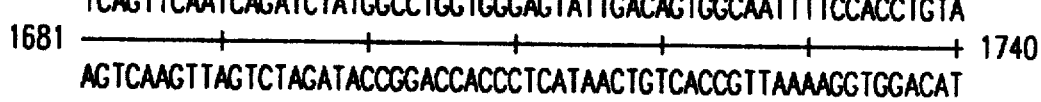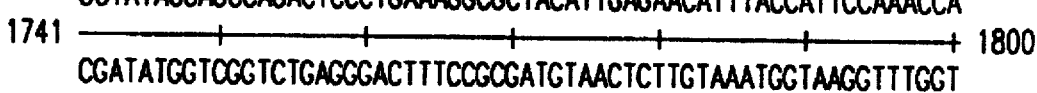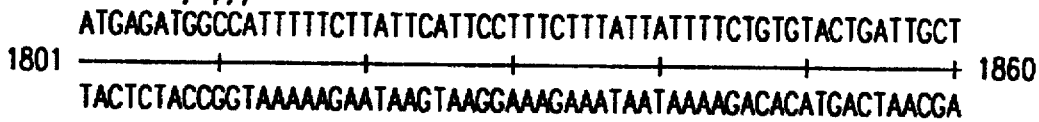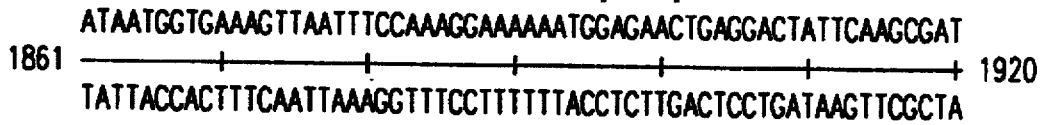
FIG.3H

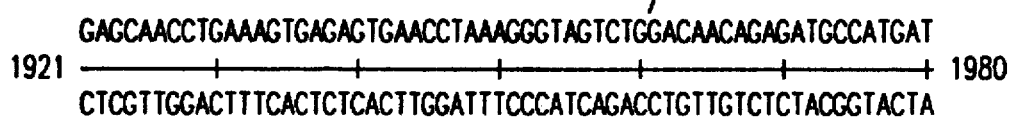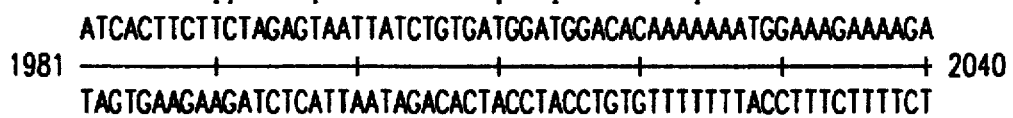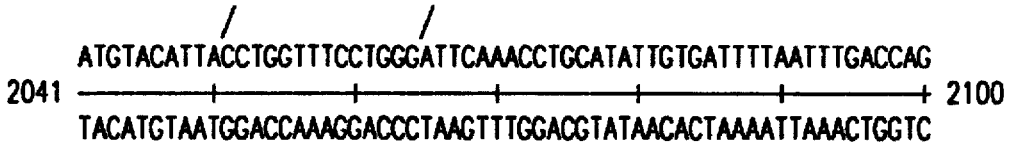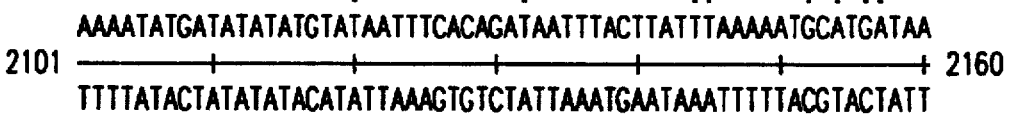
FIG. 31

```
                T
                s
                p
                A 5                    M D
                p 0                    s r
                o 9                    e a
                I I                    I I
                            /
      TGAGTTTTACATTACAAATTTCTGTTTTTTTAAAGTTATCTTACGCTATTTCTGTTGGTT
2161  ————————+————————+————————+————————+————————+————————+  2220
      ACTCAAAATGTAATGTTTAAAGACAAAAAAATTTCAATAGAATGCGATAAAGACAACCAA

T
                    s
                    p
          A         5                  N                    M
          c         0                  l                    n
          c         9                  a                    l
          l         l                  l                    l
                                       l
      AGTAGACACTAATTCTGTCAGTAGGGGCATGGTATAAGGAAATATCATAATGTAATGAGG
2221  ————————+————————+————————+————————+————————+————————+  2280
      TCATCTGTGATTAAGACAGTCATCCCCGTACCATATTCCTTTATAGTATTACATTACTCC

M
                              C  a
                    M         v  e
          R         s         i  l
          s         e         J  l
          a         l         l
          l         l
      TGGTACTATGATTAAAAGCCACTGTTACATTTCAAAAAAAAAAAAAAAAAA
2281  ————————+————————+————————+————————+————————+  2330
      ACCATGATACTAATTTTCGGTGACAATGTAAAGTTTTTTTTTTTTTTTTTT
```

Enzymes that do cut:

| | | | | | | | |
|---|---|---|---|---|---|---|---|
| AccI | AciI | AflIII | AluI | AlwI | Alw21I | AlwNI | ApaBI |
| ApoI | AvaII | BaeI | BbsI | BbvI | BccI | BcgI | BclI |
| BfaI | BglII | BpmI | Bpu10I | BsaJI | BseRI | BsgI | BsII |
| BsmI | BsmFI | Bsp1286I | Bsp1407I | BspGI | BspLU11I | BspMI | BsrI |
| BsrDI | BsrFI | BstXI | BstYI | Cac8I | CviJI | CviRI | DdeI |
| DpnI | DraI | DraIII | DrdII | EaeI | Eco57I | EcoRII | EcoRV |
| Fnu4HI | FokI | HaeI | HaeII | HaeIII | HhaI | HinfI | HphI |
| MaeII | MaeIII | MboII | MlyI | MnlI | MscI | MseI | MslI |
| MspI | MunI | MwoI | NdeI | NlaIII | NsiI | NspI | NspV |
| PleI | PstI | RcaI | RleAI | RsaI | Sau96I | Sau3AI | ScrFI |
| SexAI | SfaNI | SfcI | SspI | StuI | StyI | TaqI | TfiI |
| Tsp45I | Tsp509I | Tth111II | VspI | XbaI | XmnI | | |

FIG. 3J

Enzymes that do not cut:

| | | | | | | | |
|---|---|---|---|---|---|---|---|
| AatII | AflIII | AgeI | Alw44I | ApaI | AscI | AvaI | AvrII |
| BamHI | BanI | BanII | Bce83I | BcefI | BglI | Bpu1102I | BsaI |
| BsaAI | BsaBI | BsaHI | BsaWI | BscGI | BsiI | BsiEI | BsiWI |
| BsmAI | BspEI | BsrBI | BssHII | Bst1107I | BstEII | Bsu36I | ClaI |
| DrdI | DsaI | EagI | Eam1105I | EarI | EciI | Eco47III | Eco105I |
| EcoNI | EcoO109I | EcoRI | Esp3I | FauI | FseI | FspI | GdiII |
| HgaI | HgiEII | HincII | HindIII | HpaI | KpnI | MluI | MmeI |
| NaeI | NarI | NciI | NcoI | NheI | NlaIV | NotI | NruI |
| NspBII | PacI | Pfl1108I | PflMI | PmeI | PmlI | PshAI | Psp5II |
| Psp1406I | PvuI | PvuII | RsrII | SacI | SacII | SalI | SapI |
| ScaI | SfiI | SgrAI | SmaI | SpeI | SphI | SrfI | Sse8387I |
| SwaI | TaqII | TaqII | ThaI | Tth111I | XcmI | XhoI | |

FIG.3K

```
                                        M T
                             H          a s
                             H a        s p       M        M         C
              B              H a   B    e 4       b        M         v
              s              h e   s    l 5       o        n         i
              i              o l   l    l l       l        l         R
              l              l l   l    l l l     l        l         l
        GGCACGAGCGATTATGTTGGCGCTACCTATCAAGGGAAGATGTGTGACAAGAACTATGCA
        1———————+———————+———————+———————+———————+———————+ 60
        CCGTGCTCGCTAATACAACCGCGATGGATAGTTCCCTTCTACACACTGTTCTTGATACGT

T
                             M                s
              B    B   C     C a    H         C p
              s    c   v     v e    i T       v 5       B
              e    e   i     i l    n f       i 0       b
              R    f   R     J l    f i       R 9       v
              l    l   l     l l    l l       l l       l
                                   /
        GGAGGAGTTGCTTTGCACCCCAAAGCCGTAACTCTGGAATCACTTGCAATTATTTTAGTT
        61———————+———————+———————+———————+———————+———————+ 120
        CCTCCTCAACGAAACGTGGGGTTTCGGCATTGAGACCTTAGTGAACGTTAATAAAATCAA

B
              p
         F u N    B       N
         C n A l sP C     l  C  C            M
         A v u l 1D p v v u D  B  o M  v B a N         B     B M
         l i 4 w 0 d B u i 1 d  s  l n  i f c h        s     g w
         u J H N 2 e l l J 0 e  l  l l  J a 8 e  M     r     l o
         l l l l l l l l l l l  l  l l  l l l l  e     l     l l
          / /  / / /    /        /    / / / /   l            /
        CAGCTGCTGAGCCTCAGCATGGGGCTAGCGTATGACGACGTGAAC

```
            F   N
       A   Cn          I                              C              C
       IS  vuMP    o   B                              Av             S  v  P
       wf  i4ns    I   b                              I i            f  i  s
       Nc  RHIt    I   v                              u J            c  R  t
       II  IIII    I   I                              II             I  I  I
                /                                    /
      AACTGCAGCATGGAGGACTTTTCCAAGTTTATCACAAGTCAAAGCTCCCACTGTCTGCAG
  241 ────────┼────────┼────────┼────────┼────────┼────────┼──── 300
      TTGACGTCGTACCTCCTGAAAAGGTTCAAATAGTGTTCAGTTTCGAGGGTGACAGACGTC

D    C            C            R
       rM   v     S   v  B            I B A          M
       dw   i     f   i  c            e c c          n
       Io   J     c   J  c            A c i          I
       II   I     I   I  I            I I I          I
      AACCAGCCAACGCTACAGCCATCTTACAAGATGGCGGTCTGTGGGAATGGAGAGGTGGAA
  301 ────────┼────────┼────────┼────────┼────────┼────────┼──── 360
      TTGGTCGGTTGCGATGTCGGTAGAATGTTCTACCGCCAGACACCCTTACCTCTCCACCTT

T
              s
              pM    M                C       C                         MN
              A5b   b                v       v             A           a I
              p0o   o                i       i             c           BFea
              o91   I                J       R             i           sa I I
              III   I                I       I             I           gu I I
              /                                                        / /
      GAAGATGAAATTTGCGACTGTGGAAAGAAGGGCTGTGCAGAAATGCCCCCGCCATGCTGT
  361 ────────┼────────┼────────┼────────┼────────┼────────┼──── 420
      CTTCTACTTTAAACGCTGACACCTTTCTTCCCGACACGTCTTTACGGGGGCGGTACGACA

B
                                                 s
                                             A p N         F
              C            CN              I 1 s           n C
              Av     B  B  vI    M F       wB2 Ap    M     u v     B
              I i    p  c  ia    w a       2b8 cB    w     4 i     s
              uJ     m  c  JI    o u       1v6 i I   o     H R     i
              II     I  I  IV    I I       III II    I     I I     I
                 /                           // /
      AACCCCGACACCTGTAAGCTGTCAGATGGCTCCGAGTGCTCCAGCGGGATATGCTGCAAC
  421 ────────┼────────┼────────┼────────┼────────┼────────┼──── 480
      TTGGGGCTGTGGACATTCGACAGTCTACCGAGGCTCACGAGGTCGCCCTATACGACGTTG
```

FIG.4B

```
              E                         M T
A C C C       cC C C C                  a s
Mp v a Av   A M    ov a v a             e p
wa i c li   c n    5i c i c             I 4
oB R 8 uJ   i I    7R 8 J 8             I 5
II I I II   I I    II I I I             I I
         /
     TCGTGCAAGCTGAAGCGGAAAGGGGAGGTTTGCAGGCTTGCCCAAGATGAGTGTGATGTC
481  ————————+————————+————————+————————+————————+————————+  540
     AGCACGTTCGACTTCGCCTTTCCCCTCCAAACGTCCGAACGGGTTCTACTCACACTACAG

BMT
          C                                                 sas
     FRS  v                  B              M               tep
     osc  i                  c         B    b    H          EI4
     osc  i                  e         b    o    p          I15
     kaa  R                  f         s    I    h          III
     III  I                  I         I    I    I
      /                                                      /
     ACAGAGTACTGCAACGGCACATCCGAAGTGTGTGAAGACTTCTTTGTTCAAAACGGTCAC
541  ————————+————————+————————+————————+————————+————————+  600
     TGTCTCATGACGTTGCCGTGTAGGCTTCACACACTTCTGAAGAAACAAGTTTTGCCAGTG MNT               S
       als      T        Ba                N             B
     M eap      a        suD     AM   B    I             c
     s I14      q        t3p     Is   a    a             e
     I II5      I        YAn     we   n    I             f
     I III      I        III     II   I    V             I
                          /
     CCATGTGACAATCGCAAGTGGATCTGTATTAACGGCACCTGTCAGAGTGGAGAACAGCAG
601  ————————+————————+————————+————————+————————+————————+  660
     GGTACACTGTTAGCGTTCACCTAGACATAATTGCCGTGGACAGTCTCACCTCTTGTCGTC E    S
     c S Ba     S            CSC C        D               C
     o c suD X I A      CT   vfa v        r               Av  A
     R r t3p c a I      Ia   iac i        d               li  p
     I F YAn m N w      aq   RN8 J        I               uJ  o
     I I III I II I     II   III I        I               II  I
              /          /                                 /
     TGCCAGGATCTATTTGGCATCGATGCAGGCTTTGGTTCAAGTGAATGTTTCTGGGAGCTG
661  ————————+————————+————————+————————+————————+————————+  720
     ACGGTCCTAGATAAACCGTAGCTACGTCCGAAACCAAGTTCACTTACAAAGACCCTCGAC
```

FIG.4C

```
         T
         s
         E p                    C   H
         c 5                    A v i T
         o 0                    l i n f
         R 9                    u J f i
         I I                    I I I I
         / /                    /   /
         AATTCCAAGAGCGACATATCTGGGAGCTGTGGAATCTCTGCTGGGGATACAAGGAATGC
     721 ——————+————————+————————+————————+————————+————————+ 780
         TTAAGGTTCTCGCTGTATAGACCCTCGACACCTTAGAGACGACCCCCTATGTTCCTTACG

R B
         B    I sM              F                              M
         s    e as              o                              n
         m    A Wp              k                              l
         I    I II              I                              I
         CCACCTAATGACCGGATGTGTGGGAAAATAATATGTAAATACCAAAGTGAAAATATACTA
     781 ——————+————————+————————+————————+————————+————————+ 840
         GGTGGATTACTGGCCTACACACCCTTTTATTATACATTTATGGTTTCACTTTTATATGAT

T
         s
         p                              N           E
         5                      C       I           BcS
         0              F     A o       oN          soc
         9              a     c c       Is          oRr
         I              u     i 8       Ip          JIF
                        I     I I       II          III
                                        /           /
         AAATTGAGGTCTGCCACTGTTATTTATGCCAATATAAGCGGGCATGTCTGCCTTTCCCTG
     841 ——————+————————+————————+————————+————————+————————+ 900
         TTTAACTCCAGACGGTGACAATAAATACGGTTATATTCGCCCGTACAGACGGAAAGGGAC B         RCT      M        N
              sS        Ivo      b    B   HFl        AB
              at        eiq      o    c   pao        cs
              Jy        AJI      I    c   hul        il
              II        III      I    I   IIV        II
              /                                 /          /
         GAATATCCCCAAGGTCATAATGAGAGCCAGAAGATGTGGGTGAGAGATGGAACCGTCTGC
     901 ——————+————————+————————+————————+————————+————————+ 960
         CTTATAGGGGTTCCAGTATTACTCTCGGTCTTCTACACCCACTCTCTACCTTGGCAGACG
```

FIG. 4D

```
                      H                                          C
                      iT                                         v    M
                      nf                                         i    w
                      fi                                         J    o
                      II                                         I    I
                       /
      GGGTCAAATAAGGTTTGCCAGAATCAAAAATGTGTAGCAGACACTTTCTTGGGCTATGAT
961 ─────┼─────┼─────┼─────┼─────┼─────┼ 1020
      CCCAGTTTATTCCAAACGGTCTTAGTTTTTACACATCGTCTGTGAAAGAACCCGATACTA

E                       N                    M T
       C    c S            C     B   I                     Ma  s
       v    o c            v     sDMNoS                    be  p
       i    R r            i     osscIt                    ol  4
       R    I F            R     Jololy                    II  5
       I    I I            I     IIIIII                    II  I
                                  ///
      TGCAACCTGGAAAAATGCAACCACCATGGTGTATGTAATAACAAGAAGAACTGCCACTGT
1021 ─────┼─────┼─────┼─────┼─────┼─────┼ 1080
      ACGTTGGACCTTTTTACGTTGGTGGTACCACATACATTATTGTTCTTCTTGACGGTGACA E
                       R              H   B   c S
       B               I   M          iT  s F o c   A
       p               e   n          nf  o o R r   c
       m               A   I          fi  B u I F   i
       I               I   I          II  I I I I   I
                                       /
      GACCCCACATACTTACCTCCAGATTGTAAAAGAATGAAAGATTCATATCCTGGCGGGAGC
1081 ─────┼─────┼─────┼─────┼─────┼─────┼ 1140
      CTGGGGTGTATGAATGGAGGTCTAACATTTTCTTACTTTCTAAGTATAGGACCGCCCTCG S H
                         C               aCo   B     C  B
              F          v    B      R   uve   s     v  c
              o          i    c      s   9iI   r     i  e
              k          J    c      o   6JI   D     R  f
              I          I    I      I   III   I     I  I
                                                /
      ATTGATAGTGGCAACAAGGAAAGGGCTGAACCCATCCCTGTACGGCCCTACATTGCAAGT
1141 ─────┼─────┼─────┼─────┼─────┼─────┼ 1200
      TAACTATCACCGTTGTTCCTTTCCCGACTTGGGTAGGGACATGCCGGGATGTAACGTTCA
```

FIG.4E

```
                  M                          H          S                        S
                  a        B                 a          a               M        a
                  e   A    s       BB    C   vFHeM      BuD             aA       u
                  l   c    r       ssD   E   iools      c3p             el       3
                  l   i    B       ams   a   Jkelc      lAn             lw       A
                  l   l    l       JAa   e   lllll      lll             ll       l
                                   lll   l                /
                                     /       ///               /
      CGTTACCGCTCCAAGTCTCCACGGTGGCCATTTTTCTTGATCATCCCTTTCTACGTTGTG
1201 ─────────────+──────────────+──────────────+──────────────+──────────────+──────────────+──── 1260
      GCAATGGCGAGGTTCAGAGGTGCCACCGGTAAAAAGAACTAGTAGGGAAAGATGCAACAC
```

```
                                                                      B
                        S                                             c
               D        f                        F                    e       F
               p        a                        o                    8       o
               n        N                        k                    3       k
               l        l                        l                    l       l
      ATCCTTGTCCTGATTGGGATGCTGGTAAAAGTCTATTCCCAAAGGATGAAATGGAGAATG
1261 ─────────────+──────────────+──────────────+──────────────+──────────────+──────────────+──── 1320
      TAGGAACAGGACTAACCCTACGACCATTTTCAGATAAGGGTTTCCTACTTTACCTCTTAC
```

```
                            T
                            s
                            p       M            H                    B
               ESF          5       b            iT          SB       s
               aao          0       o            nf          pf       p
               rpk          9       l            fi          ea       G
               lll          l       l            ll          ll       l
                 /                                  /
      GATGACTTCTCAAGCGAAGAGCAATTTGAAAGTGAAAGTGAATCCAAAGACTAGTCTGGA
1321 ─────────────+──────────────+──────────────+──────────────+──────────────+──────────────+──── 1380
      CTACTGAAGAGTTCGCTTCTCGTTAAACTTTCACTTTCACTTAGGTTTCTGATCAGACCT
```

```
                              T
                    MET       s
               H    acs   M   p
               iT   eop   b   5           E
               nf   154   o   0           a
               fi   175   l   9           r
               ll   lll   l   l           l
                /
      CAGATTCCACAATGTCACAAGTAATTCTCTTCAGTGGACAGAAAAAAAAGTGGAAAAGAA
1381 ─────────────+──────────────+──────────────+──────────────+──────────────+──────────────+──── 1440
      GTCTAAGGTGTTACAGTGTTCATTAAGAGAAGTCACCTGTCTTTTTTTTCACCTTTTCTT
```

FIG.4F

```
                C                  C                    C C C                  B   C  H
                v       C          v a v                BBs vHe               a
                i       v  N       i c i                csm iaI
                J       i  s       J 8 R                coA JeI
                I       R  i       I I I                III III
                        I  I                             //   //
          AAGCCTATGCATTATCTTGCCTGAAAGTCAACCCTGCATATCGTGGTCTCCATCAGGCCA
     1441 ─────┼─────────┼─────────┼─────────┼─────────┼─────────┼ 1500
          TTCGGATACGTAATAGAACGGACTTTCAGTTCGGACGTATAGCACCAGAGGTAGTCCGGT B
                      s
                   Ap  N
                   fL  I
                   IU MaN           BN  M
                   If sfs           od' s
                   II IIp           ee  I
                   II III           II  I
                    /   /            /
          GAAATCATATCTCTCCATTACACATGTATGATACATATGTGTGTATATTATTCCATAAAT
     1501 ─────┼─────────┼─────────┼─────────┼─────────┼─────────┼ 1560
          CTTTAGTATAGAGAGGTAATGTGTACATACTATGTATACACACATATAATAAGGTATTTA T
                                  s
                                  p
                                  A5
                                  p0
                                  o9
                                  II
                                   /
          GATTTACTTGTAAGAAATGAATGATTATGAATTTCATATTATACTTTGATATTTTACCCT
     1561 ─────┼─────────┼─────────┼─────────┼─────────┼─────────┼ 1620
          CTAAATGAACATTCTTTACTTACTAATACTTAAAGTATAATATGAAACTATAAAATGGGA T
                              s
                              p
                              M5                                  C
                  B           u0          B         R             v
                  s           n9          f         s             i
                  I           II          o         o             J
                  I            /          I         I             I
          ATTTCTGGTAGTCGGTAGTCATCAATTGTATTTTCTAGTAGGTACATTATAGAAAAGGCT
     1621 ─────┼─────────┼─────────┼─────────┼─────────┼─────────┼ 1680
          TAAAGACCATCAGCCATCAGTAGTTAACATAAAAGATCATCCATGTAATATCTTTTCCGA
```

FIG.4G

```
              N
        B   IRK
        o   asp
        n   lan
        I   VII
                /
        ATAAGAAAATAAATGTGGTACCA
1681 ————————+————————+—— 1703
        TATTCTTTTATTTACACCATGGT
```

Enzymes that do cut:

| | | | | | | | |
|---|---|---|---|---|---|---|---|
| AciI | AflIII | AluI | AlwI | Alw21I | AlwNI | ApaBI | ApoI |
| BaeI | BanI | BbsI | BbvI | BccI | Bce83I | BcefI | BclI |
| BfaI | BglI | BpmI | Bpu10I | Bpu1102I | BsaI | BsaBI | BsaJI |
| BsaWI | BseRI | BsgI | BsiI | BsII | BsmI | BsmAI | Bsp1286I |
| BspGI | BspLU11I | BsrI | BsrBI | BsrDI | BstEII | BstYI | Cac8I |
| ClaI | CviJI | CviRI | DdeI | DpnI | DrdII | DsaI | EaeI |
| EarI | Eco57I | EcoRI | EcoRII | FauI | Fnu4HI | FokI | HaeI |
| HaeII | HaeIII | HhaI | HinfI | HphI | KpnI | MaeII | MaeIII |
| MboII | MnlI | MscI | MseI | MslI | MspI | MunI | MwoI |
| NciI | NcoI | NdeI | NheI | NlaIII | NlaIV | NsiI | NspI |
| NspBII | PstI | PvuII | RleAI | RsaI | SapI | Sau96I | Sau3AI |
| ScaI | ScrFI | SfaNI | SfcI | SpeI | StyI | TaqI | TaqII |
| TfiI | Tsp45I | Tsp509I | XcmI | | | | |

Enzymes that do not cut:

| | | | | | | | |
|---|---|---|---|---|---|---|---|
| AatII | AccI | AflII | AgeI | Alw44I | ApaI | AscI | AvaI |
| AvaII | AvrII | BamHI | BanII | BcgI | BcgI | BglII | BsaAI |
| BsaHI | BscGI | BsiEI | BsiWI | BsmFI | Bsp1407I | BspEI | BspMI |
| BsrFI | BssHII | Bst1107I | BstXI | Bsu36I | DraI | DraIII | DrdI |
| EagI | Eam1105I | EciI | Eco47III | Eco105I | EcoNI | EcoO109I | EcoRV |
| Esp3I | FseI | FspI | GdiII | HgaI | HgiEII | HincII | HindIII |
| HpaI | MluI | MlyI | MmeI | NaeI | NarI | NotI | NruI |
| NspV | PacI | Pfl108I | PflMI | PleI | PmeI | PmlI | PshAI |
| Psp5II | Psp1406I | PvuI | RcaI | RsrII | SacI | SacII | SalI |
| SexAI | SfiI | SgrAI | SmaI | SphI | SrfI | Sse8387I | SspI |
| StuI | SwaI | ThaI | Tth111I | Tth111II | VspI | XbaI | XhoI |
| XmnI | | | | | | | |

FIG.4H 5,693,496

DNA ENCODING THE MOUSE AND HUMAN PH30 BETA CHAIN PROTEIN

FIELD OF THE INVENTION

The present invention provides sperm surface proteins and DNA sequences encoding the proteins which are useful in the prevention of fertilization. More particularly, the cloning and characterization of the mouse and human PH30 beta chain genes, as well as their use as contraceptive vaccines, are described.

BACKGROUND OF THE INVENTION

Four methods of family planning are currently available in the U.S., sterilization, abstinence, abortion and contraception. Of these four birth control methods, contraception is the most widely utilized. Despite the substantial U.S. and global demand for contraception, the presently available methodologies fall short of market needs. Oral contraceptives and barrier methods dominate today's contraceptive market but have significant shortcomings. Oral contraceptives, though efficacious, are documented to be associated with significant side effects including increased risks of cardiovascular disease and breast cancer and are not recommended for women over the age of 35. Barrier methods, while safe, have failure rates approaching 20%. There is a clear need for increased availability of and improvements in contraceptives that offer superior safety, efficacy, convenience, acceptability and are affordable to women and men worldwide. Identification of novel approaches for controlling fertility is therefore necessary.

Immunization of male and female animals with extracts of whole sperm is known to cause infertility. [Tung, K., et al., *J. Reproductive Immunol.*, 1; 145–158 (1979); Menge, A., et al., *Biol. of Reproduction*, 20, 931–937 (1979)]. Moreover, men and women who spontaneously produce antisperm antibodies are infertile, but otherwise healthy. [Bronson, R., et al., *Fert. and Sterile*, 42, 171–183 (1984)]. Although the critical sperm antigens are unknown, these observations have led to the proposal that sperm proteins might be useful in the development of a contraceptives vaccine.

In mammalian species, sperm proteins are believed to have a role in sperm adhesion to the zona pellucida of the egg. The PH30 protein is known to be involved in sperm egg binding and antibodies that bind to PH30 inhibit this interaction. PH30 is an integral membrane protein present on posterior head of sperm which mediates sperm-oocyte fusion. The PH30 protein consists of two immunologically distinct alpha and beta subunits. Both subunits are made as larger precursors and then finally processed in epididymis where sperm become fertilization competent. [Primakoff, P., et al. *J. Cell Biology*, 104, 141–149 (1987); Blobel, C. P., et al., *J. Cell Biology*, 111, 69–78 (1990)]. Monoclonal antibodies that recognize PH30 inhibit sperm-oocyte fusion in vitro, indicating its importance in fertilization [Primakoff, P., et al., *J. Cell Biology*, 104, 141–149 (1987)].

Guinea pig PH30 alpha and beta chains have been cloned by Blobel et al. Mature PH30 alpha chain consists of 289 amino acids and encodes a transmembrane domain as well as an integral fusion peptide (82–102) that is similar to a potential fusion peptide of E2 glycoprotein of rubella virus. Guinea Pig PH30 beta chain has an open reading frame of 353 amino acids and also encodes a transmembrane domain. [Blobel C. P., et al., *Nature*, 356, 248–251 (1992)]. The predicted amino acid sequence of the PH30 beta chain protein contains significant homology to a class of proteins called disintegrins found in snake venom. These proteins are known to bind to a family of proteins called integrins and prevent their normal functioning in cell adhesion (a well studied example is platelet aggregation). The N-terminal ninety amino acids integrin binding disintigrin domain of PH30 beta has been postulated to mediate the binding of PH30 to its putative integrin receptor on oocytes. The cloning and sequence determination of the mouse and human PH30 beta chain genes would permit novel approaches to the control of sperm egg binding and fusions. These approaches include, but are not limited to, eliciting an immune response directed at all or part of the PH30 beta chain protein and using the PH30 beta chain protein as part of a screen to identify small molecules that alter sperm egg interactions.

Mammalian fertilization is, in most cases, species specific. Thus, the identification and isolation of sperm surface proteins essential for fertilization in species other than guinea pig would be useful for providing effective long lasting contraception in those species. Thus far, the lack of biochemical identification, isolation and cloning of candidate adhesion proteins of sperm has hindered scientists in developing effective contraceptives for humans as well as other mammalian species.

SUMMARY OF THE INVENTION

The instant invention relates to a sperm protein in substantially pure form selected from a human PH30 beta chain protein, a mouse PH30 beta chain protein or an amino acid sequence substantially homologous to either the human or mouse PH30 beta chain protein.

In one embodiment of the invention is the sperm protein having an integrin binding sequence which is not TDE.

In one class is the sperm protein wherein the integrin binding sequence is selected from FEE or QDE.

In a subclass is the sperm protein which is the human PH30 beta chain protein.

Illustrative of this subclass is the sperm protein having an integrin binding sequence that is FEE.

Further illustrating the invention is a DNA sequence which encodes the sperm protein or a portion of the sperm protein sufficient to constitute at least one epitope.

An illustration is the DNA sequence wherein the epitope is on the native protein.

Exemplifying the invention is the DNA sequence which encodes all or a portion of human PH30 beta chain protein.

An example of the invention is the DNA sequence, wherein the DNA encoding all or a portion of the human PH30 beta protein is s characterized by the ability to hybridize, under standard conditions, to the DNA sequence shown in SEQ ID NO: 1.

More particularly illustrating the invention is a contraceptive composition comprising a therapeutically effective amount of the protein, or a polypeptide having the substantially same amino acid sequence as a segment of the protein provided that the polypeptide is sufficient to constitute at least one epitope, and a pharmaceutically acceptable carrier.

Another illustration is the contraceptive composition wherein the epitope is on the native protein.

Further exemplifying the invention is the contraceptive composition, wherein the protein is the human PH30 beta chain protein.

More specifically illustrating the invention is the contraceptive composition, wherein the protein is produced by expressing the gene encoding an immunogenic epitope of the sperm protein in a recombinant DNA expression vector.

Specifically exemplifying the invention is a vector comprising an inserted DNA sequence encoding for the protein.

A further illustration of the invention is the vector, wherein the inserted DNA sequence is characterized by the ability to hybridize, under standard conditions, to a DNA sequence selected from the DNA sequences of SEQ ID NO: 1 or SEQ ID NO: 3.

Another example of the invention is a host that is compatible with and contains the vector.

More specifically exemplifying the invention is a method of producing a human or mouse PH30 beta chain sperm protein, comprising the steps of culturing cells containing PH30 beta chain DNA and recovering the sperm protein from the cell culture.

A further example is the method wherein the DNA encoding all or a portion of the PH30 beta chain protein is characterized by the ability to hybridize, under standard conditions, to a DNA sequence selected from the DNA sequences of SEQ ID NO: 1 or SEQ ID NO: 3.

A more specific illustration is a method of contraception in a human or mouse subject in need thereof, comprising administering to the subject an amount of the sperm protein which is effective for the stimulation of antibodies which bind to the sperm protein in vivo, thereby preventing or substantially reducing the rate of sperm-egg fusion.

Further illustrating the invention is the method wherein the sperm protein has an integrin binding sequence which is not TDE.

Another illustration is the PH30 beta chain protein made by the process described.

Another example is a DNA sequence as shown in Seq. ID No. 1 encoding human PH30 beta chain protein.

Still further illustrating the invention is a purified and isolated DNA sequence consisting essentially of a DNA sequence encoding a polypeptide having an amino acid sequence sufficiently duplicative of that of human or mouse PH30 beta to allow the possession of the biological property of initiating sperm-egg binding or promoting sperm-egg fusion. This biological activity can be determined using the in vitro sperm-oocyte binding/fusion assays [Primakoff, P., et al., *J. Cell. Biol.*, 104:141–149 (1987)].

More particularly exemplifying the invention is the DNA sequence wherein the amino acid sequence contains an integrin binding sequence which is not TDE.

BRIEF DESCRIPTION OF THE DRAWINGS

FIGS. 1A, 1B, 1C, 1D, 1E, 1F and 1G comprise is a diagram representing the human PH30 beta cDNA gene sequence encoding the human PH-30 beta protein, and the deduced amino acid sequence of the human PH-30 beta protein present in three letter code. The sequence disclosure of FIGS. 1A through 1G is represented as SEQ ID NO: 1 and 2.

FIGS. 2A, 2B, 2C, 2D and 2E comprise is a diagram representing the mouse PH30 beta cDNA gene sequence, and the deduced amino acid sequence of the mouse PH-30 beta protein present in three letter code. The sequence disclosure of FIGS. 2A through 2E is represented as SEQ ID NO: 3 and 4

FIGS. 3A, 3B, 3C, 3D, 3E, 3F, 3G, 3H, 3I, 3J and 3K represent is a restriction MAP of the human PH30 beta cDNA sequence.

FIGS. 4A, 4B, 4C, 4D, 4E, 4F, 4G and 4H represent is a restriction MAP of the mouse PH30 beta cDNA sequence.

DETAILED DESCRIPTION OF THE INVENTION

The subject invention relates to sperm surface proteins which are essential for fertilization, or portions thereof, and their use in contraceptive methods. A sperm surface protein is essential for fertilization if, for example, a monoclonal antibody to the protein or a polyclonal antibody raised against the purified protein, when bound to sperm, inhibits in vitro or in vivo fertilization or any step of in vitro fertilization. The process of fertilization is defined as the binding or fusion of two gametes (sperm and egg) followed by the fusion of their nuclei to form the genome of a new organism. The surface protein can be located in the plasma membrane of sperm and/or the inner acrosomal membrane. It can be a protein or glycoprotein. The isolated surface protein used for immunization can comprise the entire surface protein or some portion of the protein (external to the cell) which is immunogenic. Two such sperm surface proteins are the mouse and human PH30 beta chain sperm surface proteins. The PH30 beta genes encode proteins which are present on the surface of sperm cells and are essential for fertilization.

As used herein, a protein or peptide is "substantially pure" when that protein or peptide has been purified to the extent that it is essentially free of other molecules with which it is associated in nature. The term "substantially pure" is used relative to proteins or peptides with which the peptides of the instant invention are associated in nature, and are not intended to exclude compositions in which the peptide of the invention is admixed with nonproteinous pharmaceutical carriers or vehicles.

As used herein, an amino acid sequence substantially homologous to a referent PH-30 beta protein will have at least 70% sequence homology, preferably 80%, and most preferably 90% sequence homology with the amino acid sequence of a referent PH-30 beta protein or a peptide thereof. For example, an amino acid sequence is substantially homologous to mouse PH-30 beta protein if, when aligned with mouse PH-30 beta protein, at least 70% of its amino acid residues are the same. In addition, it is preferable that the substantially homologous amino acid sequence contains the integrin binding sequence.

As used herein, a DNA sequence substantially homologous to a referent PH-30 beta protein will have at least 70%, preferably 80%, and most preferably 90% sequence homology with the DNA sequence of a referent PH-30 beta. Moreover, a DNA sequence substantially homologous to a referent PH-30 beta protein is characterized by the ability to hybridize to the DNA sequence of a referent PH30 beta under standard conditions. Standard hybridization conditions are described in Maniatis, T., et al. (1989) Molecular Cloning, Cold Spring Harbor Laboratory, Cold Spring Harbor, N.Y.

An "expression vector" or "vector," as used herein, refers to a plasmid, bacteriophage, virus, or other molecule into which a gene of interest may be cloned, such that the appropriate signals for expression of that gene are present on that vector.

The term "epitope," as used herein, refers to the minimum amount of PH30 beta sequence capable of producing an efficatious, i.e., contraceptive, immune response.

The term "therapeutically effective amount," as used herein, means that amount of a drug or pharmaceutical agent that will elicit the biological or medical response that is being sought by a researcher or clinician.

Production and Purification of Immunogen

A preferred method for producing sperm surface proteins for use as a contraceptive immunogen is by recombinant DNA technology. To produce the protein using this technology it is necessary to isolate and clone DNA encoding the protein, or an immunogenic portion thereof. Those skilled in the art are familiar with a variety of approaches which can be used in an effort to clone a gene of interest. However, having nothing more than the isolated protein of interest, success in such an effort cannot be predicted with a reasonable degree of certainty.

In the Examples which follow, Applicants describe the cloning and characterization of the mouse and human PH30 beta chain genes. The mouse and human PH30 beta chain genes were isolated using a cDNA encoding the guinea pig PH30 beta chain gene. The instant invention provides specific sequence information to permit targeted intervention in controlling fertility through anti PH30 directed immune responses inhibition of sperm-egg binding and triggering of post binding signaling and effective events. These sequences permit the generation of reagents for the isolation of oocyte proteins involved in sperm-egg interaction.

The information presented in the Examples enable one skilled in the art to isolate and clone the mouse or human PH30 beta chain gene. For example, a cDNA library is prepared from testis or spermatogenic cells isolated from the mammal of interest (e.g., mouse, human). Such a cDNA library is then screened using, for example, labeled guinea pig PH30 DNA probes. DNA encoding all or a portion of human or mouse PH30 is characterized by the ability to hybridize to such a probe sequence under hybridization conditions such as those described in Example 1. Methods of labeling and screening by hybridization are well known in the art. Positive clones are analyzed, and a full length cDNA is constructed by conventional methods.

The cloned gene, or portions thereof which encode an immunogenic region of the PH30 protein, can be expressed by inserting the coding region into an expression vector to produce an expression construct. Many such expression vectors are known to those skilled in the art. These vectors contain a promoter for the gene of interest as well as additional transcriptional and translational signals. Expression vectors for both eukaryotic host cells and prokaryotic host cells are widely available. The DNA expression construct is used to transform an appropriate host cell.

Eukaryotic, in particular mammalian, host cells are often utilized for the expression of eukaryotic proteins. It has been found, for example, that eukaryotic proteins may exhibit folding problems when expressed in prokaryotic cells. In addition, production of authentic, biologically active eukaryotic proteins from cloned DNA sometimes requires post-translational modification such as disulfide bond formation, glycosylation, phosphorylation or specific proteolytic cleavage processes that are not performed in bacterial cells. This is especially true with membrane proteins. The sperm surface protein is produced using the transcriptional and translational components of the host cell. After an appropriate growth and expression period, the host cell culture is lysed and the sperm surface protein is purified from the lysate. Lysis buffers typically include non-ionic detergent, protease inhibitors, etc.

From the solubilized cell extract, the sperm surface protein can be purified and isolated by physical and biochemical methods such as ultracentrifugation, column chromatography, high performance liquid chromatography, electrophoresis, etc. Alternatively, the sperm surface protein can be isolated by affinity chromatography using monoclonal or polyclonal antibodies [see Primakoff et al., Biol. of Reprod. 38, 921-934 (1988)]. Such methods for purifying proteins are well known to those skilled in the art.

As mentioned above, antigenic portions or epitopes of the sperm surface protein are useful as immunogen, in addition to the full length protein. Antigenic fragments can be produced, for example, by proteolytic digestion of the full length protein, followed by isolation of the desired fragment. Alternatively, chemical synthesis can be used to generate the desired fragment starting with monomer amino acid residues.

With respect to the PH30 protein, certain antigenic domains are preferred candidates for use in a contraceptive vaccine. As is discussed in greater detail in the Exemplification section which follows, the PH30 β subunit contains a domain which is highly conserved when compared to a class of proteins known as disintegrins. A peptide (or portion thereof) which is identical or substantially identical to this domain is preferred for use in the contraceptive methods of this invention. Substantially identical, as used in the preceding sentence, means that at least 70% of the amino acid sequence of the peptide is identical to the corresponding portion of the PH30 β disintegrin domain.

Disintegrins are found in snake venom, for example, and are known to bind to a class of platelet surface proteins known as integrins. The binding of disintegrins to integrins has been shown to inhibit blood clotting. By analogy, peptides corresponding to the PH30 β disintegrin domain are predicted to be active in sperm-egg binding and fusion.

Contraceptive Vaccine

Once the sperm surface protein has been produced and purified, a vaccine can be produced by combining the sperm surface protein or portion thereof with a suitable carrier for administration to a subject for immunization. For successful vaccine development it is necessary that the immunogen exhibit tissue specificity, that is, it is expressed on the target tissue only and must be essential for the process of reproduction. It is known that the PH30 protein, which is expressed only on sperm, is involved in sperm egg binding and antibodies that bind to PH30 inhibit that interaction.

The cloning and characterization of human PH30 beta permits novel approaches for using PH30 as a target to control human fertility. PH30 beta protein or peptides can be used directly as an antigen to elicit an immune response directed to the whole or a relevant part of the PH30 beta chain protein. Testing of these approaches requires availability of sufficient quantities of PH30 beta protein. The cloning and sequencing of the mouse and human PH30 beta chain provides information necessary to recombinantly express all or part of the PH30 beta protein. These expressed proteins are used with or without adjuvant to immunize women or female mice. The elicited humoral immune responses are monitored by assays that use PH30 beta as antigen. Secreted antibodies in the female reproductive system will bind to the sperm head and disrupt fertilization. The availability of the recombinant mouse PH30 beta protein permits establishment of an animal model system for testing efficacy, reversibility and safety of specific methods of controlling fertility based on PH30.

A vaccine can contain one or more sperm surface proteins. Sperm surface proteins of the present invention can be combined with adjuvants which contain non-specific stimulators of the immune system. Proper use of adjuvants can induce a strong antibody response to foreign antigens (i.e., sperm surface proteins). The action of adjuvants is not fully understood, but most adjuvants incorporate two components. One is a substance designed to form a deposit which protects the antigen from catabolism. Two methods of forming a deposit are to use mineral oils or aluminum hydroxide precipitates. With mineral oils, such as Freund's adjuvant, the immunogen is prepared in a water-in-oil emulsion. For aluminum hydroxide, the immunogen is either adsorbed to preformed precipitants or is trapped during precipitation.

The second component required for an effective adjuvant is a substance that will stimulate the immune system non-specifically. These substances stimulate the production of a large set of soluble peptide factors known as lymphokines. In turn, lymphokines stimulate the activity of antigen-processing cells directly and cause a local inflammatory reaction at the site of injection. A component of lipopolysaccharide known as lipid A is commonly used. Lipid A is available in a number of synthetic and natural forms that are much less toxic than lipopolysaccharides, but still retain most of the desirable adjuvant properties of the lipopolysaccharide molecules. Lipid A compounds are often delivered using liposomes. The two bacteria that are commonly used in adjuvants as non-specific stimulants are *Bordatella pertussis* and *Mycobacterium tuberculosis*. When used as whole bacteria, they must be heat-killed prior to use. The immunomodulatory mediators of *B. pertussis* include a lipopolysaccharide component and the pertussis toxin. The pertussis toxin has been purified and is available commercially. *M. tuberculosis* is commonly found in complete Freund's adjuvant. The most active component of *M. tuberculosis* has been localized to muramyl dipeptide which is available in a number of forms.

Immunizations (Inoculation and Booster Shots)

The subject to be immunized can be any mammal which possesses a competent immune system. Examples of subject mammals include humans and domestic animals (e.g. dogs, cats, cows, horses, etc.), as well as animals intended for experimental or other purposes (e.g., mice, rats, rabbits, etc.).

Two different criteria are important to consider in determining the proper dose for the initial immunization. First, the optimum dose to achieve the strongest response and second, the minimum dose likely to induce the production of useful polyclonal antibodies. Much of the injected material will be catabolized and cleared before reaching the appropriate target immune cell. The efficiency of this process will vary with host factors, the route of injection, the use of adjuvants, and the intrinsic nature of the surface protein injected. Thus, the effective dose delivered to the immune system may bear little relationship to the introduced dose and consequently dose requirements must be determined empirically. These determinations can be readily made by one skilled in the art. Secondary injections and later boost can be given with amounts similar to or less than the primary injection.

The route of injection is guided by three practical decisions: 1) what volume must be delivered; 2) what buffers and other components will be injected with the immunogen; and 3) how quickly should the immunogen be released into the lymphatics or circulation. For example, with rabbits, large volume injections normally are given at multiple subcutaneous sites. For mice, large volumes are only possible with intraperitoneal injections. If adjuvants or particulate matter are included in the injection, the immunogen should not be delivered intravenously. If a slow release or the inoculant is desired, the injections should be done either intramuscularly or intradermally. For immediate release, use intravenous injections.

Primary antibody responses often are very weak, particularly for readily catabolized, soluble antigens. Hence, secondary or booster injections are required after the initial immunization. A delay is needed before reintroducing the protein into a primed subject. A minimum of 2 or 3 weeks is recommended but greater intervals are possible. The antibody responses to secondary and subsequent injections is much stronger. Higher titers of antibody are reached, but more importantly, the nature and quantity of the antibodies present in serum changes. These changes yield high-affinity antibodies. The intervals between secondary, tertiary and subsequent injections may also be varied, but usually need to be extended to allow the circulating level of antibody to drop enough to prevent rapid clearance of newly injected antigen.

Subsequent booster injections will be required to increase reduced circulating antibody for continued contraception. The actual intervals for these injections will differ from species to species. However, the intervals can be determined by one skilled in the art by monitoring serum levels of sperm surface protein antibodies.

In another embodiment, subjects can be administered with alloantisera, or monoclonal antibodies, directed to a sperm surface protein to achieve contraception. The alloantiserum is raised in another individual of the same species, isolated from the serum of the individual and prepared in a suitable carrier for injection into the recipient subject. Those skilled in the art are familiar with methods for preparing and formulating monoclonal antibodies for administration.

There is convincing evidence that naturally occurring antibodies to sperm cause infertility in women [Bronson, R. A., et al., *Fertility and Sterility*, 42:171–183 (1984)]. This infertility is better correlated with the antibody liters in cervical mucus than with the serum [Clark, G. N., *Amer. J Reprod. Immunol.*, 5:179–181 (1984)]. Presence of antisperm antibodies in the cervical mucus of infertile women results in poor sperm penetration through the cervical mucus and agglutination of the sperm, thereby reducing the number of sperm available for fertilization. Thus, success of a contraceptive vaccine depends in particular on the generation of mucosal immune responses involving sustained titers of anti-sperm antibodies in the female reproductive tract.

Generally, local application of the antigen is an effective way to stimulate an antibody response by that mucosa [Mestecky, J., *J Clin. Immunol.*, 7:265–276 (1987)]. However, local mucosal immunization is ineffective in female reproductive tract due to the barrier function of the luminal epithelium and to rapid loss of antigen from the lumen of reproductive tract. Stability and adhesiveness of the antigen on the mucosal surface is important for the induction of the mucosal immune responses [de Aizpurua, H. J. and Russell-Jones, G. J., *J Exp. Med.*, 167:440 (1988)]. Adhesive antigens are critical to successful mucosal immunization, not only because they are effective mucosal immunogens themselves, but also because they are carrier proteins for other antigens. Cholera toxin is a potent immunogen when given mucosally, but acts as an adjuvant when given in combination with other antigens [McKenzie, S. J. and Halsey, J. A., *J. Immunol.*, 133:1818 (1984)]. Effective immunization is also dependent on the stability of the antigen on a mucosal surface. Many antigens for use in mucosal vaccines are poorly immunogenic because they are unable to survive in the acidic and proteolytic conditions of the mucosal surface [O'Hagen, D. T., *Curr. Opin. Infect. Dis.*, 3:393 (1990)]. The DL-lactide-co-glycolide (DL-PLG) microsphere, microparticle carrier system is one of the most suitable systems for mucosal immunization. DL-PLG microspheres protect the antigen at mucosal surface and are taken up by the mucosal lymphoid tissues where they induce mucosal immunity [Eldridge, J. H. et al, *Curr. Top. Microbiol. Immunol.*, 146:59 (1989)]. Liposomes and inactivated micro-organisms also are used as microparticle carriers.

Some parenteral adjuvants such as Avridine, a lipoidal amine and muramyl dipeptide (MDP), the active component of mycobacteria in Freund's complete adjuvant, also have been shown to be active as oral mucosal adjuvants and enhance mucosal immunization [Anderson, A. O. and Reynolds, J. A., *J. Reticuloendothel. Soc.*, 26(suppl): 667 (1979); Taubman, M. A., et al., *Ann. NY Acad. Sci.*, 409:637 (1983)]. Development of mucosal immune responses in female reproductive tract are optimized by using various adjuvants, micro particle carriers, by immunizing at local or remote mucosal surfaces or by combination of parenteral and mucosal immunization.

Utility of PH30 beta in Identification of Small Molecules that will Disrupt Sperm-egg Interaction and Fertilization The comparison of the protein sequences of both mouse and human PH30 beta chain genes shows significant homology to a class of proteins called disintegrins found in the snake venoms. These proteins are known to bind a family of cell surface molecules called integrins and prevent their normal function in cell adhesion. On the basis of these homologies it is reasonable to conclude that the PH30 receptor on the oocyte is an integrin. Comparisons of the disintegrin domain sequences of guinea pig, mouse and human PH30 beta chain genes show significant differences in their putative ligand binding domain. In particular, the sequences in this region are different from other disintegrins and among the three species. The recombinant mouse and human PH30 beta proteins are used to make affinity resins to purify, identify and characterize mouse and human PH30 receptors. The recombinant PH30 beta also are used to determine its relative affinity to other integrins expressed in other tissues and are used as a ligand for cloning of the PH30 receptor.

Since the integrin recognition sequences in PH30 beta are species specific, the sequence information is necessary to identify small molecules that disrupt fertilization in a species specific manner. The recombinant mouse and human PH30 beta are used to set up screens to identify small molecules that act either as antagonist to PH30 receptor and disrupt PH30 binding or act as an agonist and stimulate PH30 receptor inducing transmembrane signaling, egg cortical granule release and zona reaction thus making the egg impenetrable for fertilization.

The present invention is further illustrated in the following exemplification.

EXAMPLE 1

Isolation of DNA Encoding Mouse and Human PH30 beta

A. cDNA Library Plating

One million independent recombinant bacteriophage from both a human testis cDNA library in λgt 11 (Clontech, Palo Alto, Calif.) and mouse testis cDNA library (Stratagene La Jolla, Calif.) in UNI-ZAP XR were plated. Plaque lifts were done in duplicate by placing a nitrocellulose filter on the plate for two minutes, and treating the filter with denaturing solution (0.5M NaOH, 1.5M NaCl), neutralization buffer (0.5M Tris pH 7.5, 1.5M NaCl) and 2×SSC (3M NaCl, 0.35M sodium citrate pH 7.0) for two minutes each. The filters were dried for thirty minutes at room temperature and then baked for two hours at 80° C. in a vacuum oven.

B. Generation of Probe

A guinea pig PH30 beta cDNA was isolated by RT-PCR (reverse transcriptase-polymerase chain reaction) as a 1020 bp (base pairs), HindIII/Bam HI fragment, containing 94% of the coding sequence. This fragment was subcloned into pBluescript SK$^+$ vector (Stratagene, La Jolla, Calif.) and verified by sequence analysis. A probe was made by nick translating the purified 1020 bp guinea pig PH30 beta fragment. The filters were probed at 42° C. for fifteen hours in hybridization solution (7 mM Tris pH 7.5, 40% formamide, 4×SSC, 0.8×Denhard's, 20 µg/ml of salmon sperm DNA and 10% Dextran sulfate) containing $10^6$ cpm (counts per minute)/ml of the labeled probe. The filters were washed twice at room temperature for fifteen minutes each with 2×SSC/0.2% SDS (sodium dodecyl sulfate), then twice at room temperature with 0.2×SSC/0.1% SDS, then once at 42° C. for 30 minutes with 0.1×SSC/0.1% SDS. The filters were exposed to XAR film (Eastman Kodak Co, Rochester, N.Y.) for 15 hours. The positive plaques were picked into 1 ml of SM (0.1M NaCl, 10 mM Magnesium Sulphate, 2% gelatin, 50 mM Tris pH 7.5) and screened again as described above. After four rounds of screening, the purified plaques were obtained.

Purified plaques of mouse testicular library were subcloned into pBluescript SK$^+$ vector using the EX ASSIT helper phage and SOLR cells (Stratagene, La Jolla, Calif.). DNA from the purified plaques of human testicular library was isolated using light PLG 2 tubes and following manufacturer's (Clontech, Palo Alto, Calif.) directions. The DNA was then digested with the restriction enzyme EcoRI and ligated into pBluescript SK$^+$ and was used to transform competent *E. coli* strain HB101 cells.

C. DNA Sequencing and Analysis

Cloned inserts were sequenced on both strands using the Sequenase kit (United States Biochemical, Cleveland, Ohio). Sequences were analyzed by searching GeneBank and EMBL DNA sequence database using the FASTA program (University of Wisconsin, Genetics Computer Group) and sequence comparisons were done using the GAP program.

D. Characterization of cDNA Clones

The screening of the mouse testicular library with a 1020 bp guinea pig PH30 beta probe resulted in the isolation of a 1.7 kb (kilo base pair) cDNA clone. This cDNA clone contains a 1371 nucleotide open reading frame and a 329 nucleotide 3' untranslated region. When mature parts of the guinea pig and mouse PH30 beta were compared, the mouse PH30 beta clone showed a maximum of 63% identity to guinea pig PH30 beta at the nucleotide level. The amino terminal 103 residues of the deduced 457 amino acid sequence represents the precursor regions of the mouse PH30 beta that are cleaved off at sperm maturation. At the amino acid level the mature mouse, and guinea pig PH30 betas were 54% identical with all the cysteines lining up.

The human testicular cDNA library screening identified a 2.331 kb cDNA which contains an open reading frame of 1959 nucleotides and 372 nucleotide 3' untranslated region. The human PH30 beta clone was 63 and 67% identical in its open reading frame to mouse and guinea pig PH30 beta genes, respectively. Comparison of the derived 653 amino acid sequence with the mouse and guinea pig PH30 beta indicates that the amino terminal 299 represents the precursor and carboxy terminal 354 amino acids represent the mature part of human PH30 beta respectively. The amino acid sequence of the mature human PH30 beta was 54% homologous to mature guinea pig and mouse PH30 beta proteins.

Protein sequence comparison of mouse and human PH30 beta to guinea pig PH30 beta and snake venom disintegrins indicated significant homology. This analysis revealed similar structural organization and indicated the presence of metalloprotease and disintegrin domains in these proteins.

Metalloprotease domains of mouse and human PH30 beta shared significant similarity with the metalloprotease domains of guinea pig PH30 beta but less similarity to the metalloprotease domain of guinea pig PH30 alpha or other disintegrins. The active site signature sequence of zinc-dependent metalloproteases is present in PH30 alpha and the snake venom disintegrins, Jararhagin and Trigramin. [Wolfsberg, T. G., et al., Proc. Natl. Acad. Sci. USA 90:10783-10797 (1993)]. Similar to guinea pig PH30 beta, the mouse and human metalloprotease domain lacks the active site signature sequence and both were 80% identical to guinea pig PH30 beta and only 30% identical to guinea pig PH30 alpha metalloprotease active site sequence. Human and guinea pig PH30 beta metalloprotease domains were 60% identical.

Similar to guinea pig PH30 beta, the mouse and human PH30 beta also contain a disintegrin domain. The disintegrin domain in mouse PH30 beta contains 91 amino acids (residues 111-202) and in human, 93 amino acids (residues 299-392). Most disintegrins of snake venom contain a consensus integrin binding sequence RGD. Another family of snake venom disintegrins that are linked to a carboxyl terminus cysteine rich domain, lack the RGD tripeptide but contain a unique tripeptide and adjacent cysteine. Guinea pig, mouse and human PH30 beta proteins also do not contain RGD tripeptide and share more similarity with this later family of disintegrins. These snake venom disintegrins and disintegrin domains of guinea pig, mouse and human PH30 beta contain a negatively charged residue at the carboxyl end of the tripeptide sequence. The integrin binding sequence of guinea pig PH30 beta is TDE. One skilled in the art would have expected that the integrin binding site of PH30 beta of other mammalian species would also be TDE. However, after isolation of human and mouse PH30 beta, it was found that this was not the case. It was unexpectedly discovered that the critical sequence at the integrin binding site was not conserved. Comparisons of guinea pig, mouse and human PH30 beta disintegrin domains showed significant variation in their putative integrin binding sequences although the carboxy terminus end of these domains were identical. The putative integrin binding residues in PH30 beta were QDE in mouse and FEE in human. These differences in the integrin binding sequences between species were an unexpected and surprising finding.

Both mouse and human PH30 beta contain an epidermal growth factor like repeat and a transmembrane domain that are 60% identical to similar regions of guinea pig PH30 beta.

EXAMPLE 2

Contraceptive Vaccination by the Administration of PH30 beta Protein

Female or male mice (about 7 weeks old at the time of first injection) receive two injections of PH30 beta in the mounts stated below. Recombinant or native PH30 beta, purified from cell line or sperm by mAb-affinity chromatography or biochemical methods, shows at least 90% purity (i.e., no more than 10% detectable contaminants) using silver-staining of purified protein on SDS gels. Purity of each PH30 preparation used for immunization of females or males is verified by SDS polyacrylamide gel electrophoresis and silver staining. The affinity-purified PH30 beta, in 0.375 ml phosphate-buffered saline (PBS) containing 3 mM octyglucoside (OG) is emulsified with 0.375 ml complete Freund's adjuvant (CFA). Each animal receives 0.1 ml of the emulsion subcutaneously in the back and 0.05 ml intramuscularly in a rear leg. About 3 weeks later, the same amount of PH30 beta in PBS and 3 mM OG is emulsified with incomplete Freund's adjuvant (IFA), and is injected in the same sites in each animal. Control females and males receive the same injections on the same schedule and containing PBS and 3 mM OG and CFA or IFA, but lacking PH30 beta. To allow the injected females to mate, about 6 weeks after the initial injection they are housed with males for 10 days. Each cage contains one male (13 weeks old), one PH30 beta immunized female, and from 2-4 control injected females. 24 hours after the grouping, females are checked visually daily for the vaginal plugs. Two weeks after the initiation of the mating the, females are removed into individual cages. After three weeks the pregnant females having litters and progeny are counted. To allow the injected males to mate, about six weeks after the initial injection, each injected male is housed with two females (10-13 weeks) for 10 days. The females and males are then separated and after an additional 3 weeks pups are counted.

EXAMPLE 3

Use of PH30 Disintegrin Peptides as Inhibitor of Sperm Fusion to Egg Plasma Membrane Peptides from the PH30 β disintegrin domain are tested for inhibition of sperm binding to the egg plasma membrane.

The fusion inhibition assay is carried out as follows. Young female mice (8-10 weeks of age) are injected with 5 units of pregnant mare's serum (PMS) in 0.9 NaCl intraperitoneally. 48 hours later, the mice are injected IP with 5 units of hCG (human chorionic gonadotrophin) in 0.9% NaCl to trigger super ovulation. 14-16 hours after hCG injection, the ovulated oocytes are collected and treated with hyaluronidase to remove cumulus cells. The zona pellucida is removed with a mixture of proteases. The zona pellucida free eggs are incubated in culture media with peptide at a specified concentration for 30 minutes [Hogan, B., et al., *Manipulating The Mouse Embryo*, 91-101, (1986)]. Sperm collected from the epididymis of male mice is capacitated by incubation and acrosome reacted as described by Fleming and Yanagimachi [*Gamete Res.* 4, 253-273 (1981)] and added to the eggs and incubated for 15 minutes. The eggs are then transferred to a sperm free culture medium and incubated for an additional 1 hour and 45 minutes. The eggs are then fixed and stained as described by Primakoff et al., [*J. Cell. Biol.* 104, 141 (1987)]. The total number of swollen sperm heads are then counted. Swollen sperm heads are an indication that the sperm and egg have fused.

On the basis of these observations, several indices are calculated. The fertilization index (F.I.) is determined by dividing the total number of swollen heads by the total number of eggs. The fertilization rate (F.R.) is the percentage of eggs fertilized. The percent inhibition is determined by dividing the fertilization index of the experimental peptide by the fertilization index of the control peptide.

The PH30 β disintegrin domain represents an epitope which is critical in sperm-egg fusion. Antibodies which bind specifically to this epitope block sperm/egg fusion.

EXAMPLE 4

Use of PH30 beta to Identify Small Molecules that will disrupt sperm-egg Interaction and Fertilization A. Identification of PH30 beta receptor antagonists Identification of compounds that specifically interfere with the binding of PH30 to their receptor on the egg, has been limited due to unavailability of the sufficient quantities of PH30 protein and normal human eggs. The availability of the rPH30 beta facilitates the identification and cloning of PH30 beta receptor integrin cDNAs. These PH30 beta receptor cDNAs are used to generate recombinant PH30 beta receptors. The alternative source of PH30 beta receptors facilitates identification of substances that affect the binding of PH30 beta to its receptors.

Using conventional methods, the Chinese Hamster Ovary cells are transfected with cDNAs encoding the PH30 beta receptor to produce a stable transformed cell which expresses human PH30 beta receptor integrin in large quantities. Such a transformed cell provides a consistent source of recombinant PH30 beta receptors and is useful in the characterization of the binding of PH30 beta to its receptor and for establishing assays to screen for compounds that inhibit PH30 binding to its receptor.

Selectivity of the compounds to PH30 beta receptor is examined by using cell lines that express other integrin receptors that contain the same beta subunit and closely related alpha chain. Compounds that specifically inhibit PH30 beta/receptor interaction are tested further in biological assays, like inhibition of sperm-egg fusion assay and egg cortical granule release assay to determine their efficacy in inhibiting fertilization.

B. Protocol for PH30 beta antagonist screen

Cells expressing PH30 beta receptor are treated with extraction buffer (50 mM Tris pH 7.6, 100 mM n-Octyl β-D-Glucopyranoside, 150 mM NaCl, 1, mM $MgCl_2$ and 1 mM $CaCl_2$) and soluble material is separated by centrifugation and stored frozen at $-80°$ C. In an assay tube the 15 µl water, 80 µl of assay buffer (125 mM Tris pH 7.6, 187.5 mM NaCl, 1.25 mM $CaCl_2$, 1.25 mM $MgCl_2$ and 1.25% BSA) and 5 µl of sample compound or control (40 µM of cold PH30 beta) are added and mixed with 50 µl of $^{125}$I-PH30 beta (final concentration 40 pM) and 50 µl of cell extract (final protein concentration 250 µg/ml). The tubes are incubated at room temperature for 1 hour. Following incubation the samples are harvested using Tomtec Mach II-6×16 cell harvester and printed filtermat cat. #1205-404. Filters are dried and counted in LKB/Wallac Beta Plate counter.

$$\% \text{ Inhibition} = \frac{CPM\text{avg total binding} - CPM\text{avg sample}}{CPM\text{avg total binding} - CPM\text{avg positive control}} \times 100$$

When % inhibition >60 and the inhibition is dose related, the sample will be considered active.

C. Sperm-Oocyte fusion assay

Young female mice (approximately 8–10 weeks of age) are injected with 5 units of pregnant mare's serum (PMS) in 0.9 NaCl intraperitoneally. 48 hours later, the mice are injected IP with 5 units of hCG (human chorionic gonadotrophin) in 0.9% NaCl to trigger super ovulation. 14–16 hours after hCG injection, the ovulated oocytes are collected and treated with hyaluronidase to remove cumulus cells. Zona pellucida is removed by treating eggs briefly with 0.1 mg/ml of chymotrypsin. Oocytes are washed with Hepes buffered culture medium and are loaded with a fluorescent stain 4',6-diamidino-2-phenylindole dihydrochloride (DAPI) by incubating at 37° C. for 30 minutes. Oocytes are then washed with medium and incubated with rPH30 beta or inhibitor compound for 30 minutes followed by another 30 minute incubation with $1\times10^4$ sperms that have been previously capacitated by incubating with calcium ionophore. After incubation, the oocytes are washed, mounted and examined by light microscopy and scored for the presence of fluorescent swollen sperm heads with associated tails in cytoplasm.

$$\text{Fertilization rate} = \frac{\text{number of eggs fused}}{\text{number of eggs tested}} \times 100 \text{ (results expressed as \% fertilization)}$$

In the absence of any inhibitor >90% oocytes are fertilized. When the sperm-oocyte fusion is inhibited >60% and the inhibition is dose related the compound will be considered active.

While the invention has been described and illustrated with reference to certain preferred embodiments thereof, those skilled in the art will appreciate that various changes, modifications and substitutions can be made therein without departing from the spirit and scope of the invention. It is intended, therefore, that the invention be limited only by the scope of the claims which follow and that such claims be interpreted as broadly as is reasonable.

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2373 base pairs
( B ) TYPE: nucleic acid
( C ) STRANDEDNESS: double
( D ) TOPOLOGY: linear ( i i ) MOLECULE TYPE: cDNA ( x i ) SEQUENCE DESCRIPTION: SEQ ID NO:1:

```
GGCCAAGATT  TTCAGAATTT  CTGCCACTAC  CAAGGGTATA  TTGAAGGTTA  TCCAAAATCT   60

GTGGTGATGG  TTAGCACATG  TACTGGACTC  AGGGGCGTAC  TACAGTTTGA  AAATGTTAGT   120

TATGGAATAG  AACCCCTGGA  GTCTTCAGTT  GGCTTTGAAC  ATGTAATTTA  CCAAGTAAAA   180

CATAAGAAAG  CAGATGTTTC  CTTATATAAT  GAGAAGGATA  TTGAATCAAG  AGATCTGTCC   240

TTTAAATTAC  AAAGCGCAGA  GCCACAGCAA  GATTTTGCAA  AGTATATAGA  AATGCATGTT   300

ATAGTTGAAA  AACAATTGTA  TAATCATATG  GGGTCTGATA  CAACTGTTGT  CGCTCAAAAA   360

GTTTTCCAGT  TGATTGGATT  GACGAATGCT  ATTTTTGTTT  CATTTAATAT  TACAATTATT   420

CTGTCTTCAT  TGGAGCTTTG  GATAGATGAA  AATAAAATTG  CAACCACTGG  AGAAGCTAAT   480
```

```
GAGTTATTAC ACACATTTTT AAGATGGAAA ACATCTTATC TTGTTTTACG TCCTCATGAT      540
GTGGCATTTT TACTTGTTTA CAGAGAAAAG TCAAATTATG TTGGTGCAAC CTTTCAAGGG      600
AAGATGTGTG ATGCAAACTA TGCAGGAGGT GTTGTTCTGC ACCCCAGAAC CATAAGTCTG      660
GAATCACTTG CAGTTATTTT AGCTCAATTA TTGAGCCTTA GTATGGGGAT CACTTATGAT      720
GACATTAACA AATGCCAGTG CTCAGGAGCT GTCTGCATTA TGAATCCAGA AGCAATTCAT      780
TTCAGTGGTG TGAAGATCTT TAGTAACTGC AGCTTCGAAG ACTTTGCACA TTTTATTTCA      840
AAGCAGAAGT CCCAGTGTCT TCACAATCAG CCTCGCTTAG ATCCTTTTTT CAAACAGCAA      900
GCAGTGTGTG GTAATGCAAA GCTGGAAGCA GGAGAGGAGT GTGACTGTGG GACTGAACAG      960
GATTGTGCCC TTATTGGAGA AACATGCTGT GATATTGCCA CATGTAGATT TAAAGCCGGT     1020
TCAAACTGTG CTGAAGGACC ATGCTGCGAA AACTGTCTAT TTATGTCAAA AGAAAGAATG     1080
TGTAGGCCTT CCTTTGAAGA ATGCGACCTC CCTGAATATT GCAATGGATC ATCTGCATCA     1140
TGCCCAGAAA ACCACTATGT TCAGACTGGG CATCCGTGTG GACTGAATCA ATGGATCTGT     1200
ATAGATGGAG TTTGTATGAG TGGGATAAA CAATGTACAG ACACATTTGG CAAAGAAGTA     1260
GAGTTTGGCC CTTCAGAATG TTATTCTCAC CTTAATTCAA AGACTGATGT ATCTGGAAAC     1320
TGTGGTATAA GTGATTCAGG ATACACACAG TGTGAAGCTG ACAATCTGCA GTGCGGAAAA     1380
TTAATATGTA AATATGTAGG TAAATTTTA TTACAAATTC CAAGAGCCAC TATTATTTAT     1440
GCCAACATAA GTGGACATCT CTGCATTGCT GTGGAATTTG CCAGTGATCA TGCAGACAGC     1500
CAAAAGATGT GGATAAAAGA TGGAACTTCT TGTGGTTCAA ATAAGGTTTG CAGGAATCAA     1560
AGATGTGTGA GTTCTTCATA CTTGGGTTAT GATTGTACTA CTGACAAATG CAATGATAGA     1620
GGTGTATGCA ATAACAAAAA GCACTGTCAC TGTAGTGCTT CATATTTACC TCCAGATTGC     1680
TCAGTTCAAT CAGATCTATG GCCTGGTGGG AGTATTGACA GTGGCAATTT TCCACCTGTA     1740
GCTATACCAG CCAGACTCCC TGAAAGGCGC TACATTGAGA ACATTTACCA TTCCAAACCA     1800
ATGAGATGGC CATTTTTCTT ATTCATTCCT TTCTTTATTA TTTTCTGTGT ACTGATTGCT     1860
ATAATGGTGA AAGTTAATTT CCAAAGGAAA AAATGGAGAA CTGAGGACTA TTCAAGCGAT     1920
GAGCAACCTG AAAGTGAGAG TGAACCTAAA GGGTAGTCTG GACAACAGAG ATGCCATGAT     1980
ATCACTTCTT CTAGAGTAAT TATCTGTGAT GGATGGACAC AAAAAAATGG AAAGAAAAGA     2040
ATGTACATTA CCTGGTTTCC TGGGATTCAA ACCTGCATAT TGTGATTTTA ATTGACCAG     2100
AAAATATGAT ATATATGTAT AATTTCACAG ATAATTTACT TATTTAAAAA TGCATGATAA     2160
TGAGTTTTAC ATTACAAATT TCTGTTTTTT TAAAGTTATC TTACGCTATT TCTGTTGGTT     2220
AGTAGACACT AATTCTGTCA GTAGGGGCAT GGTATAAGGA AATATCATAA TGTAATGAGG     2280
TGGTACTATG ATTAAAAGCC ACTGTTACAT TTCAAAAAAA AAAAAAAAA ACCATCTAAA     2340
AAAGGTAGGT AGGTAAAAGA ATTATATTAT CAA                                 2373
```

( 2 ) INFORMATION FOR SEQ ID NO:2:

( i ) SEQUENCE CHARACTERISTICS:
        ( A ) LENGTH: 651 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Gly Gln Asp Phe Gln Asn Phe Cys His Tyr Gln Gly Tyr Ile Glu Gly
 1               5                  10                  15
```

```
Tyr Pro Lys Ser Val Val Met Val Ser Thr Cys Thr Gly Leu Arg Gly
            20              25                  30
Val Leu Gln Phe Glu Asn Val Ser Tyr Gly Ile Glu Pro Leu Glu Ser
        35              40                  45
Ser Val Gly Phe Glu His Val Ile Tyr Gln Val Lys His Lys Lys Ala
    50              55                  60
Asp Val Ser Leu Tyr Asn Glu Lys Asp Ile Glu Ser Arg Asp Leu Ser
65              70                  75                          80
Phe Lys Leu Gln Ser Ala Glu Pro Gln Gln Asp Phe Ala Lys Tyr Ile
                85              90                      95
Glu Met His Val Ile Val Glu Lys Gln Leu Tyr Asn His Met Gly Ser
            100             105                 110
Asp Thr Thr Val Val Ala Gln Lys Val Phe Gln Leu Ile Gly Leu Thr
        115             120                 125
Asn Ala Ile Phe Val Ser Phe Asn Ile Thr Ile Ile Leu Ser Ser Leu
130             135                 140
Glu Leu Trp Ile Asp Glu Asn Lys Ile Ala Thr Thr Gly Glu Ala Asn
145                 150                 155                 160
Glu Leu Leu His Thr Phe Leu Arg Trp Lys Thr Ser Tyr Leu Val Leu
                165             170                 175
Arg Pro His Asp Val Ala Phe Leu Leu Val Tyr Arg Glu Lys Ser Asn
            180             185                 190
Tyr Val Gly Ala Thr Phe Gln Gly Lys Met Cys Asp Ala Asn Tyr Ala
        195             200                 205
Gly Gly Val Val Leu His Pro Arg Thr Ile Ser Leu Glu Ser Leu Ala
    210             215                 220
Val Ile Leu Ala Gln Leu Leu Ser Leu Ser Met Gly Ile Thr Tyr Asp
225             230                 235                     240
Asp Ile Asn Lys Cys Gln Cys Ser Gly Ala Val Cys Ile Met Asn Pro
                245             250                 255
Glu Ala Ile His Phe Ser Gly Val Lys Ile Phe Ser Asn Cys Ser Phe
            260             265                 270
Glu Asp Phe Ala His Phe Ile Ser Lys Gln Lys Ser Gln Cys Leu His
        275             280                 285
Asn Gln Pro Arg Leu Asp Pro Phe Phe Lys Gln Gln Ala Val Cys Gly
290             295                 300
Asn Ala Lys Leu Glu Ala Gly Glu Glu Cys Asp Cys Gly Thr Glu Gln
305                 310                 315                 320
Asp Cys Ala Leu Ile Gly Glu Thr Cys Cys Asp Ile Ala Thr Cys Arg
                325             330                 335
Phe Lys Ala Gly Ser Asn Cys Ala Glu Gly Pro Cys Cys Glu Asn Cys
            340             345                 350
Leu Phe Met Ser Lys Glu Arg Met Cys Arg Pro Ser Phe Glu Glu Cys
        355             360                 365
Asp Leu Pro Glu Tyr Cys Asn Gly Ser Ser Ala Ser Cys Pro Glu Asn
370             375                 380
His Tyr Val Gln Thr Gly His Pro Cys Gly Leu Asn Gln Trp Ile Cys
385                 390                 395                 400
Ile Asp Gly Val Cys Met Ser Gly Asp Lys Gln Cys Thr Asp Thr Phe
                405             410                 415
Gly Lys Glu Val Glu Phe Gly Pro Ser Glu Cys Tyr Ser His Leu Asn
            420             425                 430
Ser Lys Thr Asp Val Ser Gly Asn Cys Gly Ile Ser Asp Ser Gly Tyr
        435             440                 445
```

|     |     |     |     |     |     |     |     |     |     |     |     |     |     |     |
|-----|-----|-----|-----|-----|-----|-----|-----|-----|-----|-----|-----|-----|-----|-----|
| Thr | Gln | Cys | Glu | Ala | Asp | Asn | Leu | Gln | Cys | Gly | Lys | Leu | Ile | Cys | Lys |
|     | 450 |     |     |     |     | 455 |     |     |     |     | 460 |     |     |     |
| Tyr | Val | Gly | Lys | Phe | Leu | Leu | Gln | Ile | Pro | Arg | Ala | Thr | Ile | Ile | Tyr |
| 465 |     |     |     |     | 470 |     |     |     |     | 475 |     |     |     |     | 480 |
| Ala | Asn | Ile | Ser | Gly | His | Leu | Cys | Ile | Ala | Val | Glu | Phe | Ala | Ser | Asp |
|     |     |     |     | 485 |     |     |     |     | 490 |     |     |     |     | 495 |     |
| His | Ala | Asp | Ser | Gln | Lys | Met | Trp | Ile | Lys | Asp | Gly | Thr | Ser | Cys | Gly |
|     |     |     | 500 |     |     |     |     | 505 |     |     |     |     | 510 |     |     |
| Ser | Asn | Lys | Val | Cys | Arg | Asn | Gln | Arg | Cys | Val | Ser | Ser | Ser | Tyr | Leu |
|     |     | 515 |     |     |     |     | 520 |     |     |     |     | 525 |     |     |     |
| Gly | Tyr | Asp | Cys | Thr | Thr | Asp | Lys | Cys | Asn | Asp | Arg | Gly | Val | Cys | Asn |
|     | 530 |     |     |     |     | 535 |     |     |     |     | 540 |     |     |     |     |
| Asn | Lys | Lys | His | Cys | His | Cys | Ser | Ala | Ser | Tyr | Leu | Pro | Pro | Asp | Cys |
| 545 |     |     |     |     | 550 |     |     |     |     | 555 |     |     |     |     | 560 |
| Ser | Val | Gln | Ser | Asp | Leu | Trp | Pro | Gly | Gly | Ser | Ile | Asp | Ser | Gly | Asn |
|     |     |     |     | 565 |     |     |     |     | 570 |     |     |     |     | 575 |     |
| Phe | Pro | Pro | Val | Ala | Ile | Pro | Ala | Arg | Leu | Pro | Glu | Arg | Arg | Tyr | Ile |
|     |     |     | 580 |     |     |     |     | 585 |     |     |     |     | 590 |     |     |
| Glu | Asn | Ile | Tyr | His | Ser | Lys | Pro | Met | Arg | Trp | Pro | Phe | Phe | Leu | Phe |
|     |     | 595 |     |     |     |     | 600 |     |     |     |     | 605 |     |     |     |
| Ile | Pro | Phe | Phe | Ile | Ile | Phe | Cys | Val | Leu | Ile | Ala | Ile | Met | Val | Lys |
|     | 610 |     |     |     |     | 615 |     |     |     |     | 620 |     |     |     |     |
| Val | Asn | Phe | Gln | Arg | Lys | Lys | Trp | Arg | Thr | Glu | Asp | Tyr | Ser | Ser | Asp |
| 625 |     |     |     |     | 630 |     |     |     |     | 635 |     |     |     |     | 640 |
| Glu | Gln | Pro | Glu | Ser | Glu | Ser | Glu | Pro | Lys | Gly |     |     |     |     |     |
|     |     |     |     | 645 |     |     |     |     | 650 |     |     |     |     |     |     |

( 2 ) INFORMATION FOR SEQ ID NO:3:

( i ) SEQUENCE CHARACTERISTICS:
        ( A ) LENGTH: 1768 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

```
GGCACGAGCG ATTATGTTGG CGCTACCTAT CAAGGGAAGA TGTGTGACAA GAACTATGCA        60
GGAGGAGTTG CTTTGCACCC CAAAGCCGTA ACTCTGGAAT CACTTGCAAT TATTTTAGTT       120
CAGCTGCTGA GCCTCAGCAT GGGGCTAGCG TATGACGACG TGAACAAGTG CCAGTGTGGC       180
GTACCTGTCT GCGTGATGAA CCCGGAAGCG CCTCACTCCA GCGGTGTCCG GGCCTTCAGT       240
AACTGCAGCA TGGAGGACTT TTCCAAGTTT ATCACAAGTC AAAGCTCCCA CTGTCTGCAG       300
AACCAGCCAA CGCTACAGCC ATCTTACAAG ATGGCGGTCT GTGGGAATGG AGAGGTGGAA       360
GAAGATGAAA TTTGCGACTG TGGAAAGAAG GGCTGTGCAG AAATGCCCCC GCCATGCTGT       420
AACCCCGACA CCTGTAAGCT GTCAGATGGC TCCGAGTGCT CCAGCGGGAT ATGCTGCAAC       480
TCGTGCAAGC TGAAGCGGAA AGGGGAGGTT TGCAGGCTTG CCCAAGATGA GTGTGATGTC       540
ACAGAGTACT GCAACGGCAC ATCCGAAGTG TGTAAGACT TCTTTGTTCA AACGGTCAC        600
CCATGTGACA ATCGCAAGTG GATCTGTATT AACGGCACCT GTCAGAGTGG AGAACAGCAG       660
TGCCAGGATC TATTTGGCAT CGATGCAGGC TTTGGTTCAA GTGAATGTTT CTGGGAGCTG       720
AATTCCAAGA GCGACATATC TGGGAGCTGT GGAATCTCTG CTGGGGGATA CAAGGAATGC       780
CCACCTAATG ACCGGATGTG TGGGAAAATA ATATGTAAAT ACCAAAGTGA AAATATACTA       840
```

```
AAATTGAGGT CTGCCACTGT TATTTATGCC AATATAAGCG GGCATGTCTG CGTTTCCCTG        900
GAATATCCCC AAGGTCATAA TGAGAGCCAG AAGATGTGGG TGAGAGATGG AACCGTCTGC        960
GGGTCAAATA AGGTTTGCCA GAATCAAAAA TGTGTAGCAG ACACTTTCTT GGGCTATGAT       1020
TGCAACCTGG AAAAATGCAA CCACCATGGT GTATGTAATA ACAAGAAGAA CTGCCACTGT       1080
GACCCCACAT ACTTACCTCC AGATTGTAAA AGAATGAAAG ATTCATATCC TGGCGGGAGC       1140
ATTGATAGTG GCAACAAGGA AAGGGCTGAA CCCATCCCTG TACGGCCCTA CATTGCAAGT       1200
CGTTACCGCT CCAAGTCTCC ACGGTGGCCA TTTTCTTGA TCATCCCTTT CTACGTTGTG        1260
ATCCTTGTCC TGATTGGGAT GCTGGTAAAA GTCTATTCCC AAAGGATGAA ATGGAGAATG       1320
GATGACTTCT CAAGCGAAGA GCAATTTGAA AGTGAAAGTG AATCCAAAGA CTAGTCTGGA       1380
CAGATTCCAC AATGTCACAA GTAATTCTCT TCAGTGGACA GAAAAAAAAG TGGAAAAGAA       1440
AAGCCTATGC ATTATCTTGC CTGAAAGTCA AGCCTGCATA TCGTGGTCTC CATCAGGCCA       1500
GAAATCATAT CTCTCCATTA CACATGTATG ATACATATGT GTGTATATTA TTCCATAAAT       1560
GATTTACTTG TAAGAAATGA ATGATTATGA ATTTCATATT ATACTTTGAT ATTTTACCCT       1620
ATTTCTGGTA GTCGGTAGTC ATCAATTGTA TTTTCTAGTA GGTACATTAT AGAAAAGGCT       1680
ATAAGAAAAT AAATGTGGTA CCATAATAAT CAATATCATA CAACCACCAT CTAAAAAAGG       1740
TAGGTAGGTA AAAGAATTAT ATTATCAA                                          1768
```

(2) INFORMATION FOR SEQ ID NO:4:

(i) SEQUENCE CHARACTERISTICS:
        (A) LENGTH: 457 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

```
Gly Thr Ser Asp Tyr Val Gly Ala Thr Tyr Gln Gly Lys Met Cys Asp
 1               5                  10                  15

Lys Asn Tyr Ala Gly Gly Val Ala Leu His Pro Lys Ala Val Thr Leu
            20                  25                  30

Glu Ser Leu Ala Ile Ile Leu Val Gln Leu Leu Ser Leu Ser Met Gly
        35                  40                  45

Leu Ala Tyr Asp Asp Val Asn Lys Cys Gln Cys Gly Val Pro Val Cys
    50                  55                  60

Val Met Asn Pro Glu Ala Pro His Ser Ser Gly Val Arg Ala Phe Ser
65                  70                  75                  80

Asn Cys Ser Met Glu Asp Phe Ser Lys Phe Ile Thr Ser Gln Ser Ser
                85                  90                  95

His Cys Leu Gln Asn Gln Pro Thr Leu Gln Pro Ser Tyr Lys Met Ala
            100                 105                 110

Val Cys Gly Asn Gly Glu Val Glu Glu Asp Glu Ile Cys Asp Cys Gly
        115                 120                 125

Lys Lys Gly Cys Ala Glu Met Pro Pro Pro Cys Cys Asn Pro Asp Thr
    130                 135                 140

Cys Lys Leu Ser Asp Gly Ser Glu Cys Ser Ser Gly Ile Cys Cys Asn
145                 150                 155                 160

Ser Cys Lys Leu Lys Arg Lys Gly Glu Val Cys Arg Leu Ala Gln Asp
                165                 170                 175

Glu Cys Asp Val Thr Glu Tyr Cys Asn Gly Thr Ser Glu Val Cys Glu
```

|     | 180 |     |     |     |     |     | 185 |     |     |     |     |     | 190 |     |     |
| --- | --- | --- | --- | --- | --- | --- | --- | --- | --- | --- | --- | --- | --- | --- | --- |
| Asp | Phe | Phe<br>195 | Val | Gln | Asn | Gly | His<br>200 | Pro | Cys | Asp | Asn | Arg<br>205 | Lys | Trp | Ile |
| Cys | Ile<br>210 | Asn | Gly | Thr | Cys | Gln<br>215 | Ser | Gly | Glu | Gln | Gln<br>220 | Cys | Gln | Asp | Leu |
| Phe<br>225 | Gly | Ile | Asp | Ala | Gly<br>230 | Phe | Gly | Ser | Ser | Glu<br>235 | Cys | Phe | Trp | Glu | Leu<br>240 |
| Asn | Ser | Lys | Ser | Asp<br>245 | Ile | Ser | Gly | Ser | Cys<br>250 | Gly | Ile | Ser | Ala | Gly<br>255 | Gly |
| Tyr | Lys | Glu | Cys<br>260 | Pro | Pro | Asn | Asp | Arg<br>265 | Met | Cys | Gly | Lys | Ile<br>270 | Ile | Cys |
| Lys | Tyr | Gln<br>275 | Ser | Glu | Asn | Ile | Leu<br>280 | Lys | Leu | Arg | Ser | Ala<br>285 | Thr | Val | Ile |
| Tyr | Ala<br>290 | Asn | Ile | Ser | Gly | His<br>295 | Val | Cys | Val | Ser | Leu<br>300 | Glu | Tyr | Pro | Gln |
| Gly<br>305 | His | Asn | Glu | Ser | Gln<br>310 | Lys | Met | Trp | Val | Arg<br>315 | Asp | Gly | Thr | Val | Cys<br>320 |
| Gly | Ser | Asn | Lys | Val<br>325 | Cys | Gln | Asn | Gln | Lys<br>330 | Cys | Val | Ala | Asp | Thr<br>335 | Phe |
| Leu | Gly | Tyr | Asp<br>340 | Cys | Asn | Leu | Glu | Lys<br>345 | Cys | Asn | His | His | Gly<br>350 | Val | Cys |
| Asn | Asn | Lys<br>355 | Lys | Asn | Cys | His | Cys<br>360 | Asp | Pro | Thr | Tyr | Leu<br>365 | Pro | Pro | Asp |
| Cys | Lys<br>370 | Arg | Met | Lys | Asp | Ser<br>375 | Tyr | Pro | Gly | Gly | Ser<br>380 | Ile | Asp | Ser | Gly |
| Asn<br>385 | Lys | Glu | Arg | Ala | Glu<br>390 | Pro | Ile | Pro | Val | Arg<br>395 | Pro | Tyr | Ile | Ala | Ser<br>400 |
| Arg | Tyr | Arg | Ser | Lys<br>405 | Ser | Pro | Arg | Trp | Pro<br>410 | Phe | Phe | Leu | Ile | Ile<br>415 | Pro |
| Phe | Tyr | Val | Val<br>420 | Ile | Leu | Val | Leu | Ile<br>425 | Gly | Met | Leu | Val | Lys<br>430 | Val | Tyr |
| Ser | Gln | Arg<br>435 | Met | Lys | Trp | Arg | Met<br>440 | Asp | Asp | Phe | Ser | Ser<br>445 | Glu | Glu | Gln |
| Phe | Glu<br>450 | Ser | Glu | Ser | Glu | Ser<br>455 | Lys | Asp |     |     |     |     |     |     |     |

What is claimed is:

1. A DNA molecule consisting of a DNA sequence which encodes a sperm protein wherein the sperm protein is human PH30 beta chain protein consisting of SEQ. ID NO. 2 or mouse PH30 beta chain protein consisting of SEQ. ID NO. 4.

2. The DNA molecule of claim 1 wherein the DNA sequence encodes the human PH30 beta chain protein consisting of SEQ. ID NO. 2.

3. The DNA of claim 1 wherein the DNA sequence encodes the mouse PH30 beta chain protein consisting of SEQ. ID NO. 4.

4. A DNA consisting of the DNA sequence as shown in SEQ. ID NO. 1.

5. A DNA consisting of the DNA sequence as shown in SEQ. ID NO. 3.

6. A vector comprising the DNA sequence of claim 1.

7. A transformed host cell comprising the vector of claim 6.

8. A method of producing a human or mouse PH30 beta chain sperm protein, comprising culturing the transformed host cell of claim 7 and recovering the sperm protein.

* * * * *